United States Patent
Phillips et al.

(10) Patent No.: US 6,923,813 B2
(45) Date of Patent: Aug. 2, 2005

(54) DEVICES FOR CREATING VOIDS IN INTERIOR BODY REGIONS AND RELATED METHODS

(75) Inventors: Frank M. Phillips, Northbrook, IL (US); Richard W. Layne, Sunnyvale, CA (US); Bryce Anton Way, San Jose, CA (US); Derek S. Rothwell, Los Altos, CA (US); Alberto Ruiz Cantu, San Francisco, CA (US); Avram Allan Edidin, Sunnyvale, CA (US); Mark A. Reiley, Piedmont, CA (US); Arie Scholten, Manteca, CA (US)

(73) Assignee: Kyphon Inc., Sunnyvale, CA (US)

(*) Notice: Subject to any disclaimer, the term of this patent is extended or adjusted under 35 U.S.C. 154(b) by 0 days.

(21) Appl. No.: 10/892,824

(22) Filed: Jul. 16, 2004

(65) Prior Publication Data

US 2005/0113838 A1 May 26, 2005

Related U.S. Application Data

(60) Provisional application No. 60/499,934, filed on Sep. 3, 2003.

(51) Int. Cl.$^7$ .............................................. A61B 17/56
(52) U.S. Cl. ............................ 606/86; 606/79; 606/80; 606/192
(58) Field of Search ............................ 606/79, 80, 84, 606/110, 167, 170, 172, 180, 190–192, 205, 606/207, 198

(56) References Cited

U.S. PATENT DOCUMENTS

| | | |
|---|---|---|
| 3,181,533 A | 5/1965 | Health |
| 3,640,280 A | 2/1972 | Slanker et al. |
| 3,828,790 A | 8/1974 | Curtiss et al. |
| 4,203,444 A | 5/1980 | Bonnell et al. |
| 4,573,448 A | 3/1986 | Kambin |
| 4,601,290 A | 7/1986 | Effron et al. |
| 4,644,951 A | 2/1987 | Bays |
| 4,969,888 A | 11/1990 | Scholten et al. |
| 5,015,255 A | 5/1991 | Kuslich |
| 5,062,845 A | 11/1991 | Kuslich et al. |
| 5,100,423 A | 3/1992 | Fearnot |
| 5,108,404 A | 4/1992 | Scholten et al. |
| 5,242,461 A | 9/1993 | Kortenbach et al. |

(Continued)

FOREIGN PATENT DOCUMENTS

| | | |
|---|---|---|
| DE | G 88 00 197.0 | 1/1986 |
| FR | 99 15288 | 12/1999 |
| WO | WO 96/39970 | 12/1996 |
| WO | WO 01/28439 | 4/2001 |

Primary Examiner—David O. Reip
(74) Attorney, Agent, or Firm—Ryan Kromholz & Manion, S.C.

(57) ABSTRACT

Several embodiments of cutting tips for tools for creating voids in interior body regions are provided. The cutting tips provide for rotational and translational cutting. An actuator mechanism for deploying a cutting tip converts the rotational movement of a wheel into translational movement of a plunger rod. The actuator mechanism provides positive cutting action as the cutting tip is moved from a first, non-deployed position to a second, deployed position and from the second, deployed position to the first, non-deployed position. Methods of creating a void in bone provide one or more mechanical cutting tools that may be used in combination with one or more expandable void-creating structures to form a void of a desired size and configuration.

39 Claims, 22 Drawing Sheets

U.S. PATENT DOCUMENTS

| | | |
|---|---|---|
| 5,269,785 A | 12/1993 | Bonutti |
| 5,397,320 A | 3/1995 | Essig et al. |
| 5,437,665 A | 8/1995 | Munro |
| 5,439,464 A | 8/1995 | Shapiro |
| 5,445,639 A | 8/1995 | Kuslich et al. |
| 5,496,330 A | 3/1996 | Bates et al. |
| 5,499,981 A | 3/1996 | Kordis |
| 5,509,919 A | 4/1996 | Young |
| 5,536,267 A | 7/1996 | Edwards et al. |
| 5,540,693 A | 7/1996 | Fisher |
| 5,571,098 A | 11/1996 | Domankevitz et al. |
| 5,582,618 A | 12/1996 | Chin et al. |
| 5,658,280 A | 8/1997 | Issa |
| 5,730,704 A | 3/1998 | Avitall |
| 5,814,044 A | 9/1998 | Hooven |
| 5,827,289 A | 10/1998 | Reiley et al. |
| 5,827,312 A | 10/1998 | Brown et al. |
| 5,876,399 A | 3/1999 | Chia et al. |
| 5,879,353 A | 3/1999 | Terry |
| 5,891,147 A | 4/1999 | Moskovitz et al. |
| 5,925,039 A | 7/1999 | Landingham |
| 5,928,239 A | 7/1999 | Mirza |
| 5,957,884 A | 9/1999 | Hooven |
| 5,972,015 A | 10/1999 | Scribner et al. |
| 5,984,937 A | 11/1999 | Morse et al. |
| 6,015,406 A | 1/2000 | Goble et al. |
| 6,048,346 A | 4/2000 | Reiley et al. |
| 6,066,154 A | 5/2000 | Reiley et al. |
| 6,241,734 B1 | 6/2001 | Scribner et al. |
| 6,248,110 B1 | 6/2001 | Reiley et al. |
| 6,425,887 B1 | 7/2002 | McGuckin et al. |
| 6,440,138 B1 | 8/2002 | Reiley et al. |
| 6,468,279 B1 | 10/2002 | Reo |
| 6,575,919 B1 | 6/2003 | Reiley et al. |
| 6,607,544 B1 | 8/2003 | Boucher et al. |
| 6,641,587 B2 | 11/2003 | Scribner et al. |
| 6,645,213 B2 | 11/2003 | Sand et al. |
| 6,679,886 B2 | 1/2004 | Weikel et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,746,451 B2 | 6/2004 | Middleton et al. |
| 2001/0041896 A1 | 11/2001 | Reiley et al. |
| 2002/0026195 A1 | 2/2002 | Layne et al. |
| 2002/0082608 A1 | 6/2002 | Reiley et al. |
| 2002/0099385 A1 | 7/2002 | Ralph et al. |
| 2002/0156482 A1 | 10/2002 | Scribner et al. |
| 2002/0169471 A1 | 11/2002 | Ferdinand |
| 2002/0191487 A1 | 12/2002 | Sand |
| 2003/0032929 A1 | 2/2003 | McGuckin, Jr. |
| 2003/0032963 A1 | 2/2003 | Reiss et al. |
| 2003/0050644 A1 | 3/2003 | Boucher et al. |
| 2003/0233096 A1 | 12/2003 | Osorio et al. |
| 2004/0092948 A1 | 5/2004 | Stevens et al. |

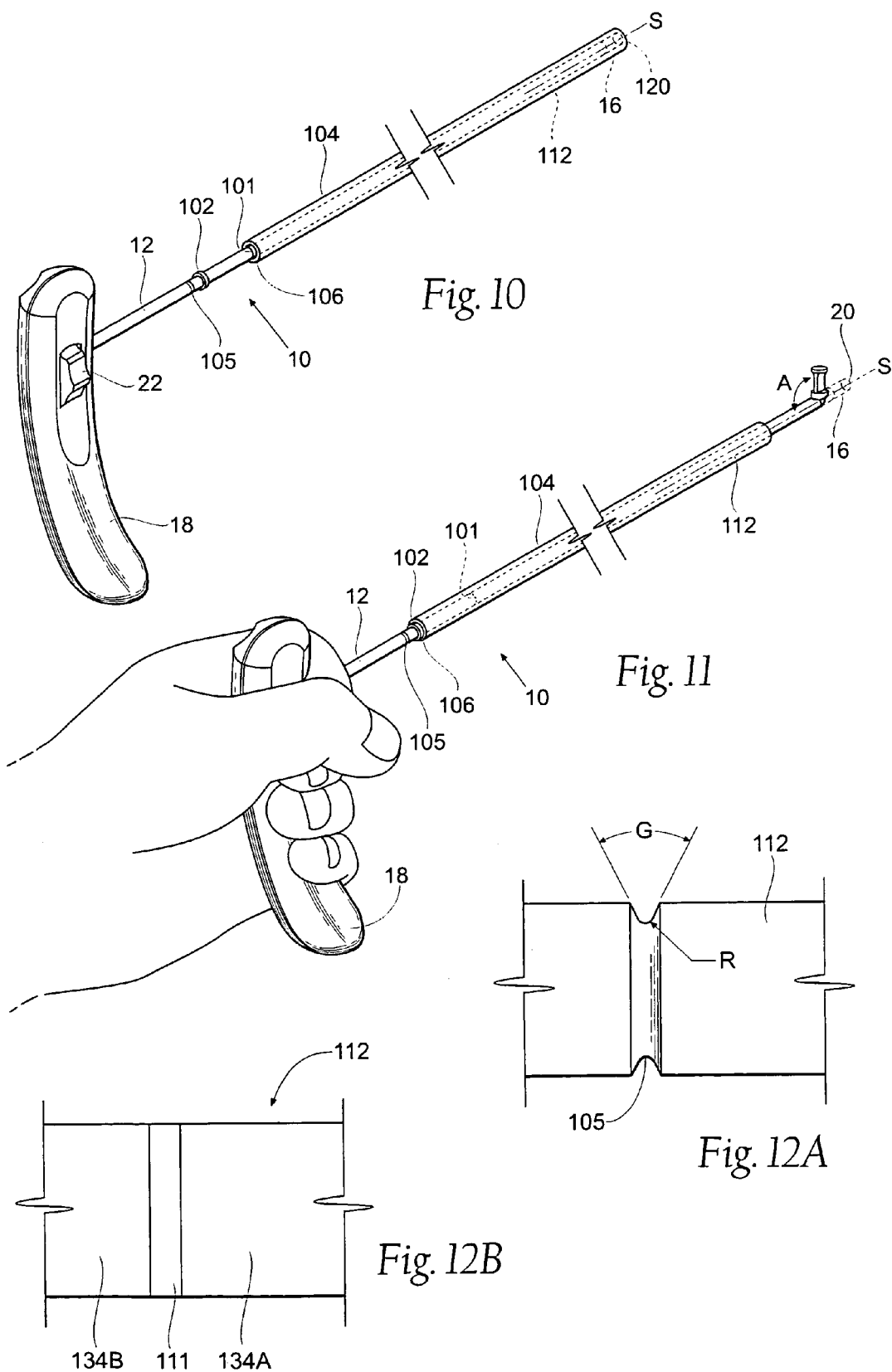

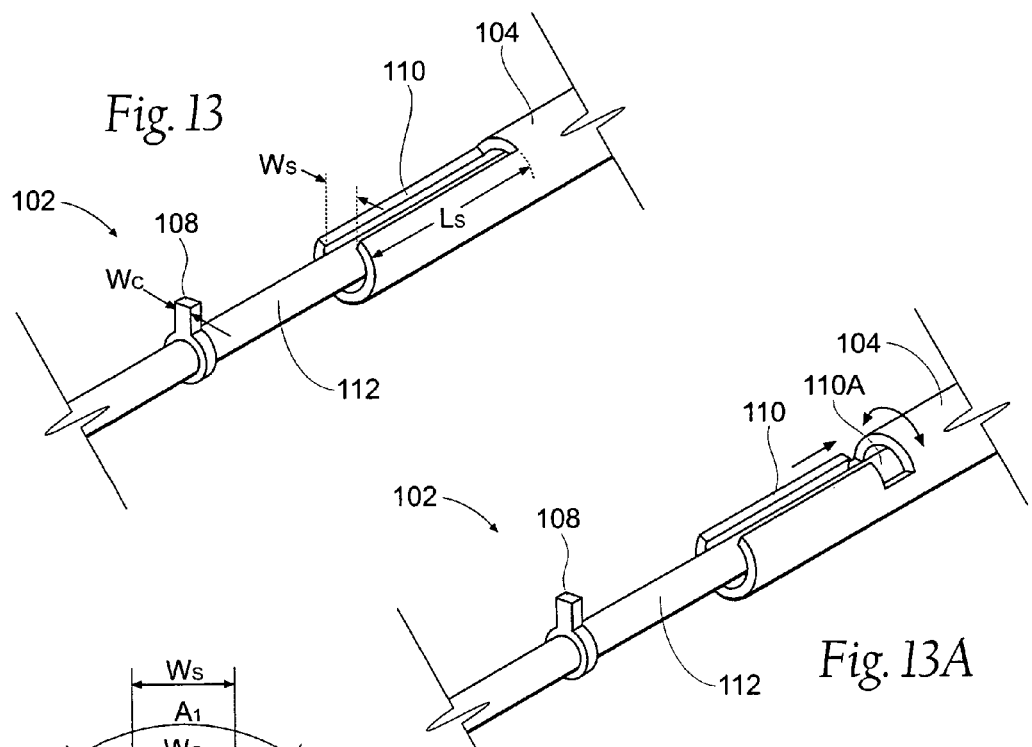
Fig. 13
Fig. 13A
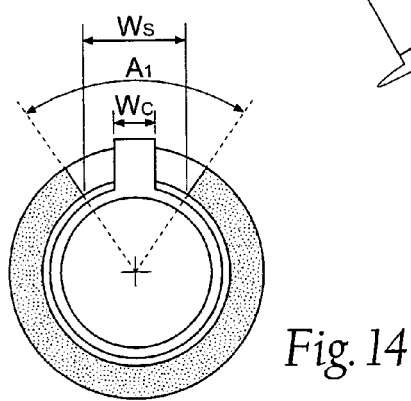
Fig. 14
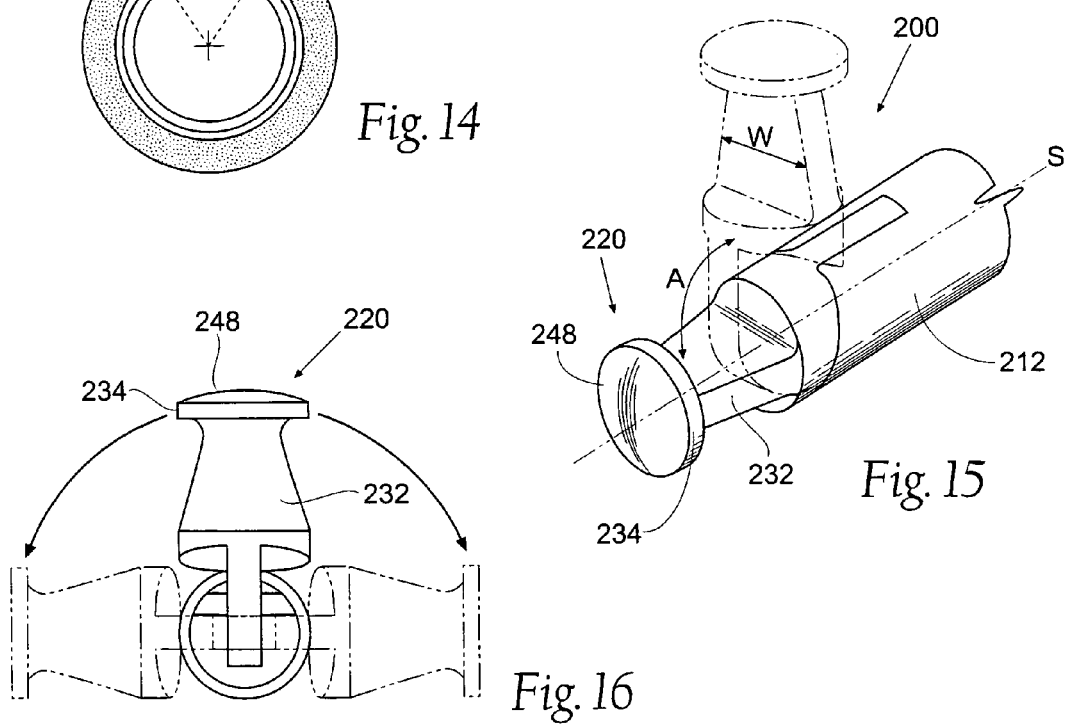
Fig. 15
Fig. 16

DEVICES FOR CREATING VOIDS IN INTERIOR BODY REGIONS AND RELATED METHODS

RELATED APPLICATION

This application claims the benefit of provisional U.S. Application Ser. No. 60/499,934, filed Sep. 3, 2003, and entitled "Mechanical Devices for Creating Voids in Interior Body Regions and Related Methods."

FIELD OF THE INVENTION

This invention relates generally to tools for creating cavities or voids in interior body regions. In particular, the invention relates to creating voids in bone for diagnostic or therapeutic purposes.

BACKGROUND OF THE INVENTION

A minimally invasive method of forming a cavity or void within one of the body's solid organs, for both diagnostic and treatment purposes, is becoming increasingly important as radiological and other types of scanning techniques improve a physician's ability to view inside the body without having to make an incision.

The most common solid organ currently making use of a minimally invasive technique to form a void is bone. Typically this is any pathological bone in the body with a fracture, osteoporosis, or a tumor. The most commonly used void-forming method for bones is the inflatable bone tamp, as described in U.S. Pat. Nos. 4,969,888 and 5,108,404. Void formation in this case is usually followed by filling with a filling substance like bone cement or a bone substitute.

Mechanical methods are also available for making voids inside solid organs. Those solid organs include the brain, the kidneys, the spleen, the liver and bone. In the brain, for example, an abscess could be easily debrided and irrigated with a minimally invasive mechanical void technique. A fractured spleen could be approached with a minimally invasive technique, to make a small void to fill with gelfoam or some other coagulant to stop hemorrhage. An osteoporotic, fractured vertebral body or bone tumor could be approached by a minimally invasive mechanical system in order to create a cavity or void and then refill with a bone substitute. A demand exists for systems or methods that are capable of forming voids in bone and other interior body regions in safe and efficacious ways.

SUMMARY OF THE INVENTION

The invention provides systems and methods for creating voids in interior body regions.

One aspect of the invention provides a cutting tip for cutting or scraping bone. In one embodiment, a curette-type instrument at the end of a shaft can be mechanically angled into different positions to scrape material to form a void. In another embodiment, a mechanical device at the end of a shaft resembles a T-type configuration and allows both translational and rotational cutting to form a void. In a third embodiment, the cutting tip includes a turned and tapered trunk. In a fourth embodiment, the cutting tip includes a conical trunk. In a fifth embodiment, a sharp, stout, metal spring is provided on the end of a shaft. In a sixth embodiment, the distal end of a shaft carries two or more fingers to grab tissue for extraction. In a seventh embodiment, a hinged void-forming device is carried by a shaft and allows for formation of a void, which may be of a rectangular or any other pre-determined shape.

Another aspect of the invention provides an actuator mechanism for deploying a cutting tip. In one embodiment, rotational movement of a thumbwheel is converted to translational movement of a plunger rod. In an alternative embodiment, rotational movement of a control knob is converted to translational movement of a plunger rod through interaction of a series of gears.

Another aspect of the invention provides a tool for creating voids in interior body regions. The tool comprises a shaft, a tip for contacting bone, and a hinge member coupling the tip to the shaft. The tip becomes uncoupled if the torque applied exceeds a maximum hinge torque. The shaft includes a region of weakness proximal to the tip along which the shaft will break if the torque applied exceeds a maximum shaft torque. The maximum hinge torque is greater than the maximum shaft torque.

According to another aspect of the invention, a tool for creating voids in interior body regions comprises a shaft assembly including a lumen, a tip for contacting bone coupled to the shaft, and a rod slidable within the lumen. The rod is tethered to the tip.

According to another aspect of the invention, a tool for creating voids in interior body regions comprises a shaft including a lumen, and a tip for contacting bone coupled to the shaft by a coupling element. The tip is additionally tethered to the shaft such that the tip remains tethered to the shaft if the coupling element becomes inoperable.

According to another aspect of the invention, a tool for creating voids in interior body regions comprises a cannula and a shaft. The shaft has a handle and is sized and configured for passage through the cannula. A projection extends radially from the shaft to restrict forward advancement of the shaft within the cannula.

Another aspect of the invention provides methods of creating a void in bone. The methods provide one or more mechanical cutting tools that may be used in combination with one or more expandable void-creating structures to form a void of a desired size and configuration.

BRIEF DESCRIPTION OF THE DRAWINGS

FIG. 10 is a perspective view illustrating the use of a marker band to identify the position of the cutting tip in relation to the distal end of the cannula.

FIG. 11 is a perspective view illustrating use of a stop to limit translational advancement of the shaft within a cannula.

FIG. 12A is an enlarged view of a groove located on the shaft of the cutting tool.

FIG. 12B is a perspective view of an alternative embodiment of a shaft in which a portion of the shaft is formed of a material of reduced strength and/or rigidity relative to the rest of the shaft.

FIG. 13 is a perspective view of an alternative embodiment of a stop that limits translational and rotational movement of the shaft along and within the cannula.

FIG. 13A is a perspective view of an alternative embodiment of a T-shaped slot that limits translation and rotational movement of the shaft along and within the cannula.

FIG. 14 is a schematic view representing the preset size and configuration of a void formed by performing a full sweep motion of a cam follower along a cam surface.

FIG. 15 is a perspective view of an alternative embodiment of a cutting tip and illustrating pivoting movement of the tip in phantom.

FIG. 16 is a front plan view of the tip shown in FIG. 15 and illustrating rotational movement of the cutting tip.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

The systems and methods embodying the invention can be adapted for use virtually in any interior body region, where the formation of a cavity or void within tissue is required for a therapeutic or diagnostic purpose. The preferred embodiments show the invention in association with systems and methods used to treat bones. This is because the systems and methods which embody the invention are well suited for use in this environment. It should be appreciated that the systems and methods which embody features of the invention can be used in other interior body regions, as well.

Various embodiments of cutting tips are described below in detail. In each case their sizes and shapes could be produced to fit the ideal void to be formed, whether it is a void in a tibia or a vertebral body. In addition, these mechanical tools could be made of any bio-compatible metal (for example, but not limited to stainless steel, titanium, titanium alloys, tantalum, aluminum, aluminum alloys, or other metals) that has adequate shear and tensile strength to perform their void-forming function. Plastic polymers having suitable biomechanical properties may also be used for these tools. Alternatively, the tool may be plated or coated with a biocompatible material.

I. Mechanical Cutting Tool

A. Curette

Figure 1:
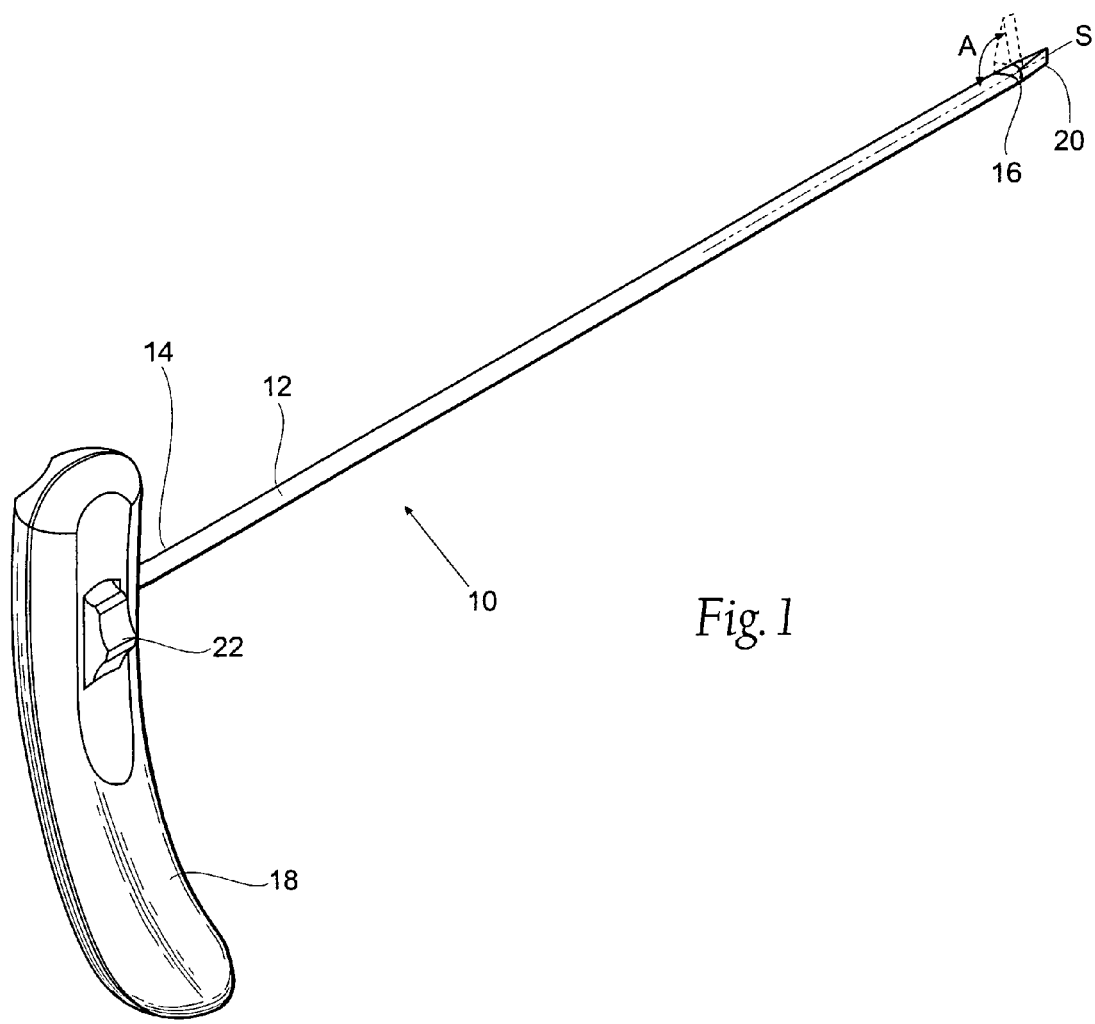
FIG. 1 is a perspective view of a mechanical tool for creating voids in interior body regions and illustrating pivoting movement of the cutting tip in phantom.
Figure 2:
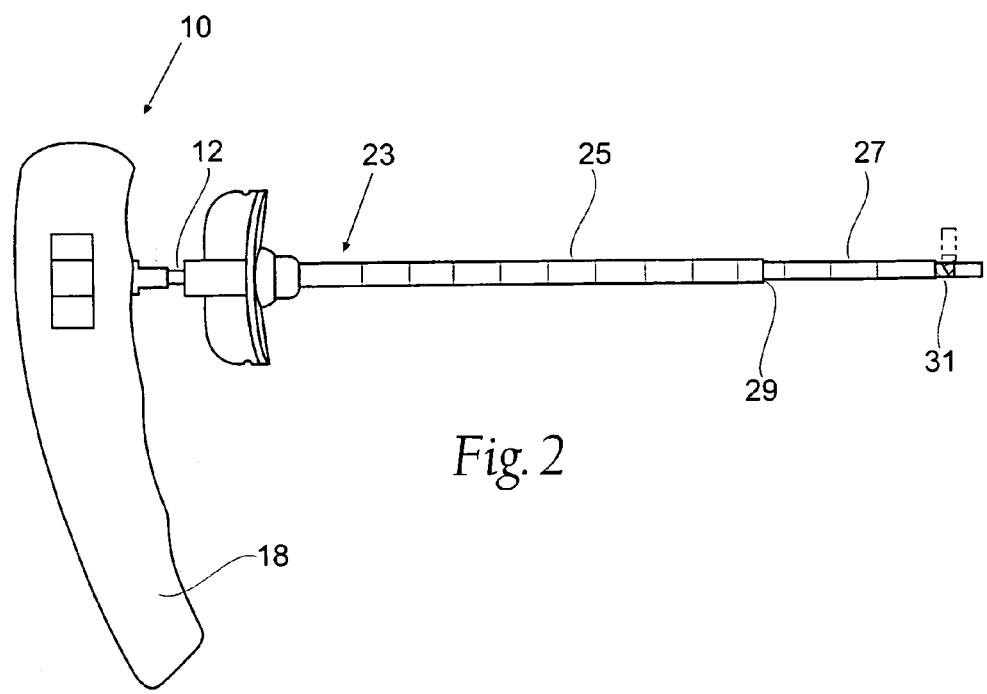
FIG. 2 is a perspective view of a bone treatment device.
Figure 3:
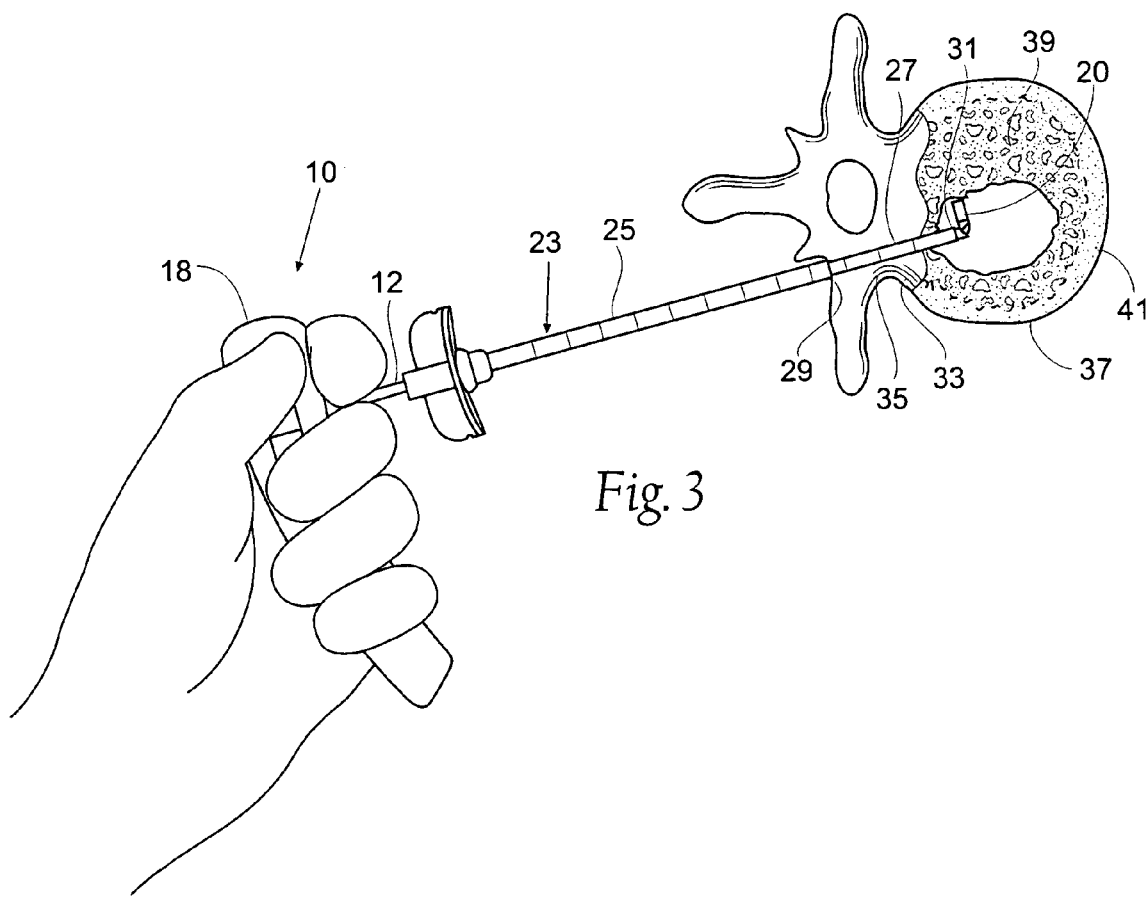
FIG. 3 is a perspective view illustrating insertion and use of the device of FIG. 2 in a vertebra.

FIGS. 1–3 show a tool 10 capable of forming a cavity or void in a targeted treatment area. The tool 10 comprises a shaft 12 having a proximal and a distal end, respectively 14 and 16. The shaft 12 preferable includes a handle 18 to aid in gripping and maneuvering the shaft 12 through a pre-formed access path into bone. The handle 18 can be made of any suitable material, e.g., any rigid polymer or metal or combination thereof, secured about the shaft 12. The handle 18 is desirably sized and configured to be securely and comfortably grasped by the physician.

The shaft 12 carries a void-forming structure 20 at its distal end 16. In the illustrated embodiment, the structure 20 takes the form of a multi-faceted cutting tip 20. The cutting tip 20 may be adapted for use in various body regions, e.g., to create a void in bone. The cutting tip 20 may also serve to remove hard or soft tumors from tissue. As used in this specification, a cutting tip is a surface adapted to mechanically form a void in bone through contact with the bone, e.g., by cutting, shearing, scooping, shaving, sciving, dissecting, or scoring of the bone.

The cutting tip 20 is hingedly coupled to distal end 16 of the shaft 12. The cutting tip 20 is desirably adapted to extend radially from the shaft 12 and radially from the pre-formed access path to a diameter that is greater than a diameter of the access path. The cutting tip 20 can be made of any suitable biocompatible material, e.g., stainless steel, cobalt chromium, titanium and alloys or mixtures thereof. The shaft 12 and cutting tip 20 can alternatively be made of different materials (e.g. alloys of stainless steel with different strengths: 303 stainless steel, 304 stainless steel, 17–4 stainless steel, 17–7 stainless steel) and welded or otherwise bonded together. As will be described in detail later, an actuator, e.g., wheel 22 (see also, e.g., FIGS. 19 and 23), permits selective movement of the cutting tip 20 from a first, closed or non-deployed position to a second, open or deployed position.

In the closed position (represented by solid lines in FIG. 1), the cutting tip 20 extends from the distal end 16 of the shaft 12 along the axis S of the shaft 12. In this position, the shaft 12 can be easily passed through a cannula 23 or other instrument. The hinge mechanism permits pivoting of the tip 20 at an angle A transverse to axis S of shaft 12 to the opened position (represented in phantom in FIG. 1). In a preferred embodiment, the cutting tip 20 is adapted to pivot and be selectively secured in any pivot position from 0–90° relative to the axis S of the shaft 12.

Desirably, the actuating mechanism provides positive, controlled movement in both directions (i.e., from the open, deployed position to the closed, non-deployed position and from the closed, non-deployed position to the open, deployed position) during all degrees of actuation. That is, the secured pivot position and angle A are maintained regardless of the rotational orientation of the shaft 12. The actuator mechanism provides positive cutting action as the tip is actuated in either direction to provide bi-directional cutting. Actuation may be repeated so as to provide continuous cutting. The speed of actuation may be varied to vary the speed of cutting. The cutting tip 20 also permits translational (i.e., longitudinal) movement along the axis S of the shaft 12 in a push-pull or sawing motion with the tip in the deployed position. The physician creates a desired void by repeated actuation, translational movement, or by performing a series of combined actuation and translational movements.

In use, the cutting tip 20 is placed in the closed position extending from the distal end 16 of the shaft 12, i.e., at a 0° angle A relative to axis S. The tool 10 may be introduced into a targeted treatment site through an open procedure. Desirably, the tool 10 is introduced in a closed and minimally invasive procedure in which a percutaneous cannula 23 is advanced into a desired treatment region, e.g., a vertebral body 37. The shaft 12 is then passed through the cannula 23 and the cutting tip 20 is extended beyond the distal end of the cannula 23. Alternatively, the cannula 23 may be removed after introduction of the tool 10. Fluoroscopy or other visualization techniques may be employed to aid in introducing the cannula 23 and tool into the targeted treatment area. The cutting tip 12 is then pivoted to a desired position, i.e., preferably any position between 0–150°, and most preferably about 90°. Also, conceivably the tip 20 could deploy in either direction without stopping in the non-deployed condition. Actuation may be repeated and the shaft 12 advanced in fore and aft directions by pushing and pulling in a sawing-like motion to thereby create a void.

If rotational cutting is desired, turning of shaft 12 is required to reposition the tip 20 to continue cutting. In this case, the cutting tip 20 is returned to the closed position and the shaft 12 turned or rotated to a new position. The cutting tip 20 is again pivoted to a desired angle A (open position) and the shaft 12 again advanced in fore and aft directions using a push-pull motion. It is apparent that the shaft 12 may be repositioned any number of times to produce a void of a desired configuration.

With reference now to FIGS. 2 and 3, the cannula 23 desirably incorporates a distal portion having a reduced profile. The cannula 23 includes a large diameter portion 25, a small diameter distal portion 27, and a transition portion 29. Alternatively, the cannula 23 may provide a taper between the large and small diameter portions 25 and 27 (not shown). The shaft 12 of the tool 10 is desirably sized to fit within a lumen 31 extending through the cannula 23, and may be of a constant or varying size.

Desirably, the reduced distal tip diameter of the cannula 23 will allow the tip of the tool 10 to be inserted into the targeted bone, with a corresponding reduction in the size of the access path created in the bone. The smaller diameter section 27 of the cannula 23 will pass through the cortical wall into the bone, while the larger diameter section 25 can abut against the outside of the bone (sealing the opening, if desired), and will desirably stretch, but not tear, softer tissues.

In a preferred embodiment, the smaller diameter portion 27 is desirably sized such that, when the larger diameter portion 25 abuts the cortical bone 33 of the pedicle 35, the distal end of the smaller diameter portion 27 extends through the pedicle 35 and emerges into the vertebral body 37 and enters into cancellous bone 39. In this embodiment, the tool 10 could be sized such that, when fully inserted into the cannula 23, the distal cutting tip 20 would be prevented from contacting and/or breaching the anterior cortical wall 41 of the vertebral body 37 or targeted bone.

Other low profile bone access tools are described in U.S. patent application Ser. No. 09/952,014, filed Sep. 11, 2001, entitled "Systems and Methods for Accessing and Treating Diseased or Fractured Bone Employing a Guide Wire," which is herein incorporated by reference.

B. T-Tip Embodiment

In many cases, it is desirable to cut in both a rotational as well as in a translational direction. In such cases, it is preferable that the rotational cutting motion reflects an ergonomic and natural motion for the physician. FIGS. 4–9 illustrate an embodiment of a cutting tool 100 having a cutting tip 120 which permits translational, rotational, or simultaneous translational and rotational movement of the cutting tip using an ergonomic and natural motion. The cutting tip is made from any suitable biocompatible material, e.g., stainless steel.

Figure 4:
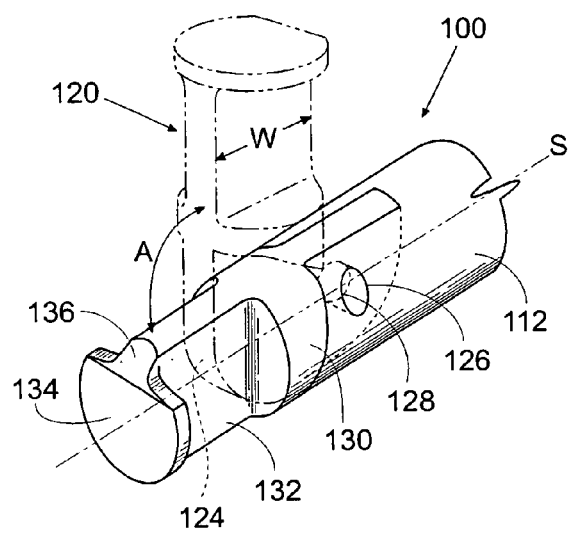
FIG. 4 is a perspective view of an alternative embodiment of a cutting tip and illustrating pivoting movement of the tip in phantom.

As FIG. 4 illustrates, the cutting tip 120 provides a pivot region 124 hingedly attached to a shaft 112, e.g., pivot pin 126 passes through hole 128 in pivot region 124 and into shaft 112. This arrangement permits a wide range of pivot motion allowing the cutting tip to pivot at virtually any desired angle. In a preferred embodiment, the cutting tip 120 is adapted to pivot from 0–90° relative to the axis S of the shaft 112. Similar to the embodiment of FIG. 1, the actuating mechanism is positive in both directions.

A collar 130 divides the pivot region 124 and a trunk region 132 and provides additional strength and support to the cutting tip 120. The maximum width (W) of the trunk 132 is parallel to the axis S of the shaft 112 when the tip 120 is deployed at 900 (illustrated in phantom in FIG. 4).

The trunk 132 carries a cutting disc 134 providing a dual rounded cutting surface extending on either side of the trunk 132, providing a 360° cutting surface. In a preferred embodiment, the diameter of disc 134 is approximately the same as the diameter of the shaft 112 so as to minimize stress on the tip 120 during cutting and to provide ease of passage through a cannula.

The tip includes a flat or straight cutting surface 136 along the tip of the disc 134 that provides greater ease in cutting bone on the pullback motion. When pushing, the shaft 112 provides the strength and force for cutting.

The disc 134 and trunk 132 together provide a large surface contact area that enables the tip 120 to take an aggressive bite into bone and gouge bone material in large chunks.

Figure 5:
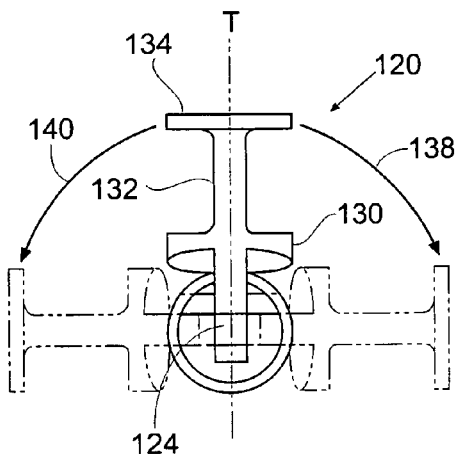
FIG. 5 is a front plan view of the tip shown in FIG. 4 and illustrating rotational movement of the cutting tip.

The disc configuration allows rotational cutting in both clockwise and counterclockwise directions. With reference to FIG. 5, the tip 120 is extended to a desired angle A, e.g., 90° along axis T. The shaft 112 is then rotated 0–90° in a first direction (represented by arrow 138) relative to axis T. The shaft 112 can be rotated 0–90° in the opposite direction (represented by arrow 140) relative to axis T to create a void extending 180° by a simple turning of the physician's wrist.

Figure 6:
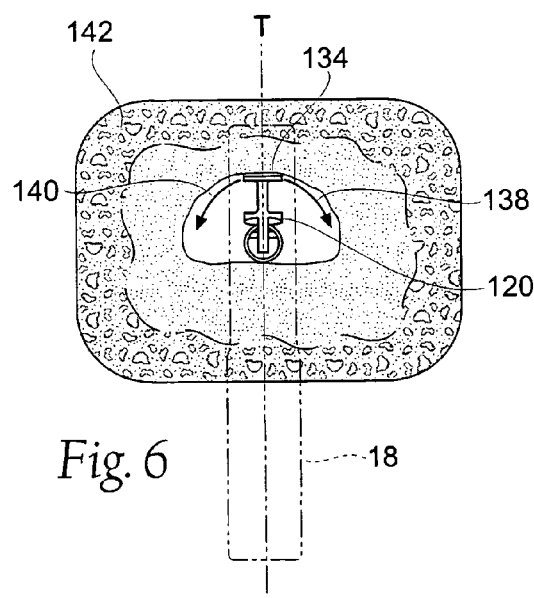
FIG. 6 illustrates 180° rotational movement of the cutting tip in a vertebra to create a 180° void.
Figure 7:
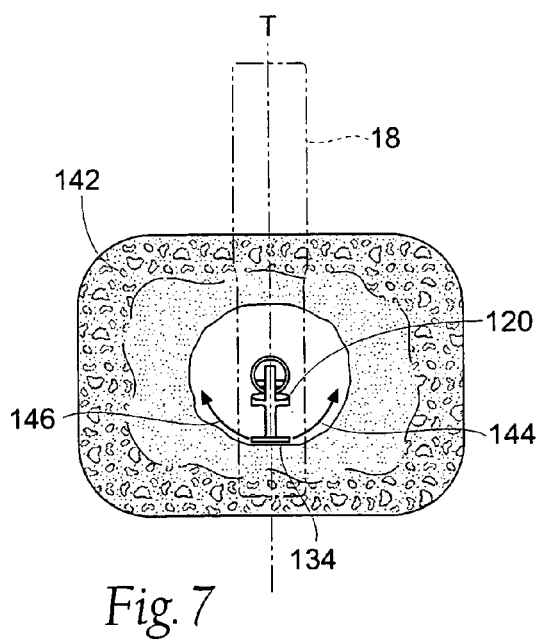
FIG. 7 illustrates the shaft rotated 180° relative to FIG. 6 and the cutting tip again rotated 180° to form a 360° void.

FIG. 6 illustrates rotation of the cutting tip 120 in bone, e.g., a vertebra 142, to create a 180° void. In many cases, it may be desirable to create a void extending 360°. As FIG. 7 shows, after formation of a 180° void, the shaft 112 may be rotated 180° and again aligned approximately along axis T. The shaft 112 is then rotated 0–90° in a first direction (represented by arrow 144) relative to axis T. The shaft 112 can be rotated 0–90° in the opposite direction (represented by arrow 146) relative to axis T to create a void extending 360°. The physician can monitor the position of the tip 120 with use of fluoroscopy.

Figure 8:
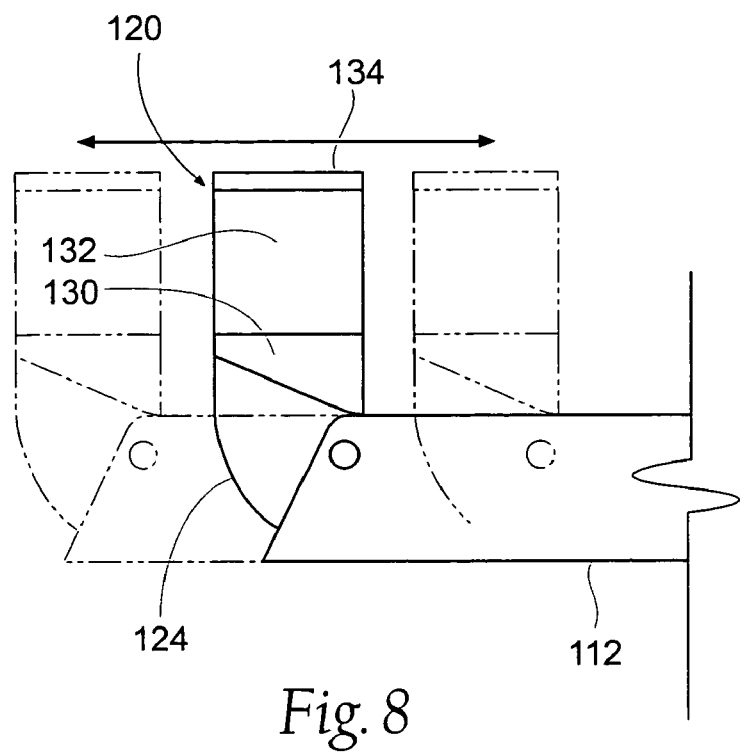
FIG. 8 is a side view of the tip shown in FIG. 4 and illustrating translational movement of the cutting tip in a sawing-like motion.
Figure 9:
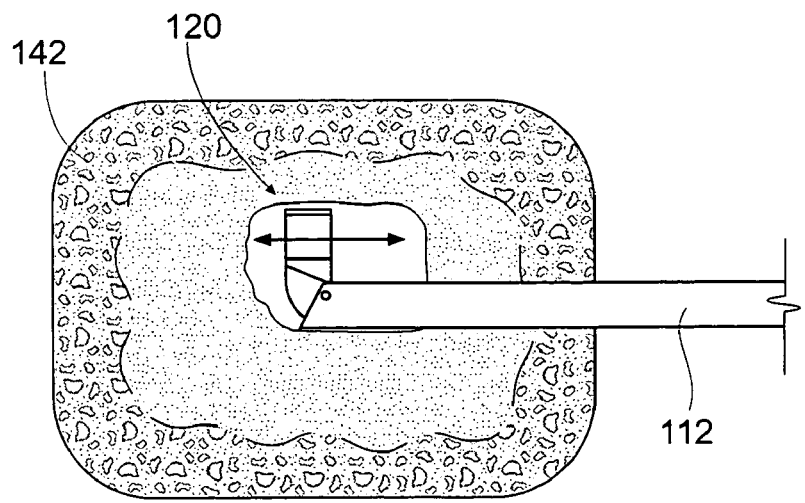
FIG. 9 illustrates the translational movement of the cutting tip and formation of a void in a vertebra.

The disc configuration also allows translational cutting in a push-pull or sawing motion as represented by arrows in FIGS. 8 and 9. In use, the physician may deliver translational and rotational forces simultaneously by pushing in and pulling out while simultaneously rotating a handle or alternating rotational and translational motions. In this manner, the physician controls rotational and translational movement of the cutting tip 120 to create a void of desired size and shape, e.g., cylindrical.

Desirably, as seen in FIG. 10, the shaft 112 carries a boss or stop 102 designed to limit forward, i.e., translational, motion of the shaft 112 within a cannula 104. The diameter of the stop 102 approximates the diameter of the cannula 104 so that the stop 102 rests against the face or top 106 of the cannula 104 to stop forward advancement of the shaft 112 within the cannula 104.

The stop 102 is positioned on the shaft 112 such that there is sufficient room to accommodate the physician's fingers wrapped around and under the handle 18. The stop 102 thus provides clearance between the physician's fingers and the percutaneous access cannula 104, preventing pinching or catching of the physician's fingers. The stop 102 stops insertion of the shaft 112 to leave a comfortable working distance for the physician's hand when rotating the shaft 112 (i.e., a sweeping cutting motion) or when using a push-pull cutting motion or a combination of both cutting motions. In a representative embodiment, the stop 102 is positioned approximately 1.75 inches (about 4.5 cm.) from the base of the handle 18. By restricting or preventing further advancement of the shaft 112, the stop 112 prevents advancement of the shaft 112 (and void-forming structure 20) within the vertebral body. This prevents the possibility of puncturing or breaching the anterior cortical wall of the vertebra 142 (see also FIG. 9).

Desirably, a marker band 101 is positioned distal of the stop 102. As seen in FIG. 10, when the shaft 112 is fully inserted into the access cannula 104, the marker band 101 is aligned with the face 106 of the cannula 104 as the cutting tip 120 is exiting the cannula 104 into a bone, e.g., a vertebra 142. As shown in FIG. 11, when the shaft 112 is fully inserted into the cannula 104, the tip 120 extends beyond the distal end 103 of the cannula 103.

In a representative embodiment, the marker band 101 is located approximately 3 cm. distal of the stop 102. In this embodiment, when the shaft 112 is fully inserted into the cannula 104 (i.e., resting against the stop 102), the tip 120 extends approximately 3.5 cm. from the distal end 103 of the cannula 104 when the cutting tip 120 is in the non-deployed position (i.e., aligned with the axis S of the shaft 112), and approximately 3 cm. from the distal end 103 of the cannula 104 when the tip 120 is in the deployed position (e.g., at 90°).

In a preferred embodiment, a groove 105 is positioned proximal the stop 102. As best seen in FIG. 12, the groove 105 is a turned angular cut having an angle G with a radius R on the shaft 112 to define a line of weakness on the shaft 112. In a representative embodiment, the groove 105 is a 60° angular cut (i.e., G= approximately 60°) having a radius R of approximately 0.006' inch. The mean torque required for failure of the shaft 112 at groove 105 (the maximum shaft torque) is less than the torque required for failure of the shaft 112 at pin 126 (the maximum hinge torque) (see also FIG. 4), or more generally, of the cutting assembly itself. For example, it has been found that the mean torque required to scrape normal bone is approximately 2.0 in.-lb. In a representative embodiment, the mean torque required for failure of the shaft 105 at groove 105 is approximately 7.3 in.-lb. and the mean torque required for failure at pin 128 is 9.3 in.-lb. In the event that excessive torque is translated through the shaft 112, the groove 105 results in the shaft 112 breaking or severing at the groove 112 before the tip 120 breaks or fails at the pivot region 124. This provides an additional safety feature that allows the shaft 112 and undeformed pivot region 124 to be safely removed from the cannula 104 without complications. Failure or deformation of the pivot region 124 is avoided.

It is contemplated that the region of weakness can also be formed by any of a variety of other suitable means that provide that the shaft 112 will sever or break prior to the tip 120 becoming uncoupled from the shaft 112 (i.e., that provide that the maximum hinge torque is greater than the maximum shaft torque). For example, as shown in FIG. 12B, a portion 111 of the shaft 112 may be formed of a material of reduced strength and/or rigidity relative to the remaining portions 113A and 113B of the shaft 112 to define a region of weakness. In one representative embodiment, shaft portions 113A and 113B are formed of a biocompatible metal and shaft portion 111 is formed of a biocompatible plastic material.

With reference to FIG. 13, the shaft 112 may also carry a boss or stop 102 with a tine or lug 108 that selectively mates with a complementary slot or groove 110 in a cannula 104 or other access device so as to limit rotational motion to a preset angle. In this arrangement, the slot or groove 110 defines a cam surface. The tine or lug 108 serves as a cam follower. The configuration of the cam surface and cam follower can vary, but preferably define a system in which a sweep of the cam follower across the full range of motion of the cam surface consistently creates a void of a predetermined size and shape.

FIG. 13 shows an embodiment in which the cam surface takes the form of an elongated slot 110 in the circumferential margin of the cannula 104. The depth of reach is defined by the depth of the slot. That is, the length LS of the slot limits forward advancement of the stop 102 (and therefore the shaft 112) within the cannula 104. The width WS of the slot is greater than the width WC of the lug or tine 102 by a pre-determined amount. The angle of rotation is controlled by the extent of the slot 110, i.e., the difference in width between the slot 110 and the width of tine or lug 108 (i.e., the difference between WS and WC). Because the depth of the reach and the angle of rotation are pre-determined and constant, a sweep of the full range of motion of the cam surface and the cam follower consistently creates a void of a predetermined size and shape. For example, FIG. 14 illustrates the formation of a pre-determined pie-shaped void having an angle Al. The pre-determined void has a length corresponding to the length LS of slot 110 as shown in FIG. 13. The slot 110 can be varied, e.g., by varying the width of the slot 110 along its length, to form voids of a desired, pre-determined shape and size. For example, FIG. 13A illustrates an alternative embodiment of a slot 110A in which the slot 110A is generally T-shaped and adapted to form a pre-determined void biased such that the most forward portion is of greater volume, with each volume also being wedge shaped.

In use, the tool 100 is introduced into a targeted treatment site. Desirably, the tool 100 is introduced in a closed and minimally invasive procedure in which a percutaneous cannula 104 is advanced into a desired treatment region, e.g., a vertebral body. Introduction of the tool may be assisted by conventional visualization techniques, as previously described. The shaft 112 is then passed through the cannula 104 and the cutting tip 120 is extended beyond the distal end of the cannula 104. The cutting tip 112 is then pivoted to the desired position, i.e., any position between 0–90°.

The physician manipulates the cutting tip 120 by sweeping the shaft 112 along the full range of motion of the cam surface and cam follower. The stop 102 serves to limit translational movement of the shaft 112 along the cannula 104 and the lug or tine 108 limits rotational movement of the shaft 112 within the cannula 104 to create a void of a pre-determined size and shape. Because the void created is of a consistent and pre-determined size and shape, visualization is not required during cutting and void formation. The need for fluoroscopy or other visualization techniques is thereby reduced, limiting the patient's exposure to radiation or dyes. Upon completion of the procedure, the cutting tip 112 is returned to the non-deployed position and the cannula 104 and tool 100 are withdrawn.

C. Turned and Tapered Trunk Embodiment

FIGS. 15 and 16 illustrate an alternative embodiment of a tool 200 for creating voids in interior body regions. In this embodiment, the trunk 232 is tapered and rotated 90° relative to the embodiment shown in FIGS. 4–9 so that the maximum width W of the trunk is perpendicular to the axis S of the shaft 212 when the tip 220 is deployed at a 90° angle A from the axis S of the shaft 212.

This arrangement minimizes the combined surface area of the disc 234 and trunk 232 in contact with the bone during scraping and cutting and thus minimizes transmission of significant force and stress to the hinge mechanism.

The disc 234 has a convex front surface 248 providing a dome-shape. Preferably, the disc 234 has a diameter that is approximately the same as the diameter of the shaft 212, minimizing stress on the tip 220 during cutting and providing ease of passage of the tip 220 through a cannula. The domed configuration facilitates cutting and scraping of bone by producing leverage on the bone that allows the tip 220 to roll out of the bone easily. The domed configuration allows the tip to easily release from bone and to disengage from the bone for easy withdrawal.

The disc 234 provides a 360° cutting surface and permits both translational and rotational movement of the cutting disc 234 when deployed at the desired angle A, as previously described.

D. Conical Trunk Configuration

Figure 17:
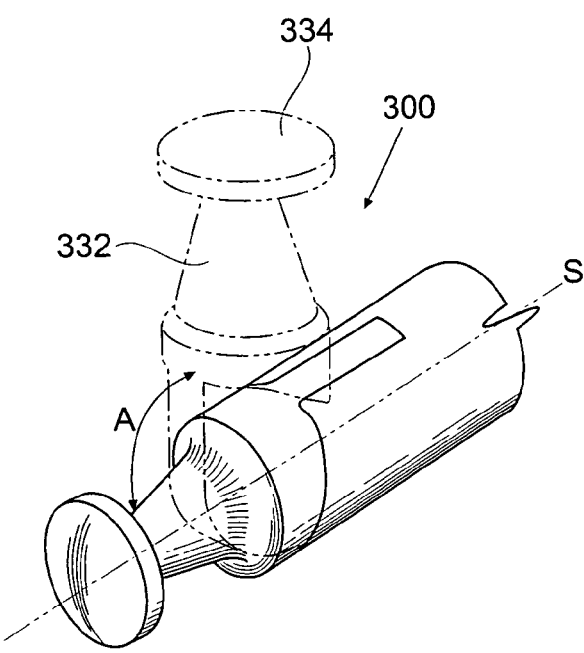
FIG. 17 is a perspective view of an alternative embodiment of a cutting tip and illustrating pivoting movement of the tip in phantom.
Figure 18:
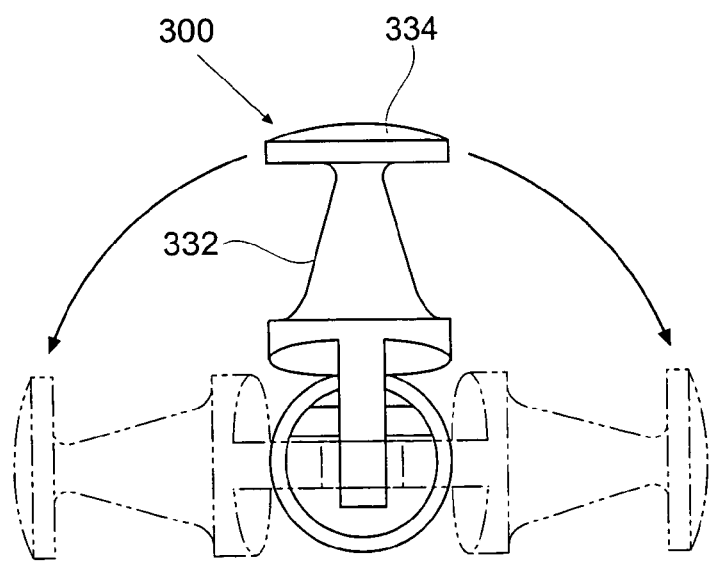
FIG. 18 is a front plan view of the tip shown in FIG. 17 and illustrating rotational movement of the cutting tip.

FIGS. 17 and 18 illustrate another alternative embodiment of a tool 300 for creating voids in interior body regions. In this embodiment, the trunk 332 is tapered similar to the embodiment of FIGS. 15 and 16, but is conical.

The trunk 332 also carries a dome-shaped disc 334 allowing both translational and rotational cutting, similar to the embodiment of FIGS. 15 and 16.

The combined cutting surface of the disc 334 and trunk 332 is minimized and is designed to reduce the force and stress on the hinged mechanism by minimizing the contact area in the bone in all directions. The same profile (symmetrical cross-section of the conical trunk 332) is presented to the bone regardless of whether pushing or pulling (translational) force, turning (rotational) force, or a combination of both forces is applied.

II. Actuator Mechanism

A. Thumbwheel Embodiment

FIGS. 19–22 illustrate one embodiment of an actuator mechanism for use with a void-forming tool. The actuator mechanism converts rotational motion into translational movement to control the deployment of a cutting tip. By way of illustration and not limitation, the actuator mechanism is illustrated with the cutting tip 120 embodiment of FIGS. 4–9.

The actuator mechanism provides a thumbwheel 150, an insert or cap 152, flange 154, plunger rod 156, and rotational stop 158. The thumbwheel 150, cap 152, flange 154, plunger rod 156, and stop 158 may be made of any suitable metal. The thumbwheel is seated in a free-floating manner in a slot 160 within handle 18. In a preferred embodiment, the handle 18 is made of a strong and durable polymer plastic.

Figure 19:
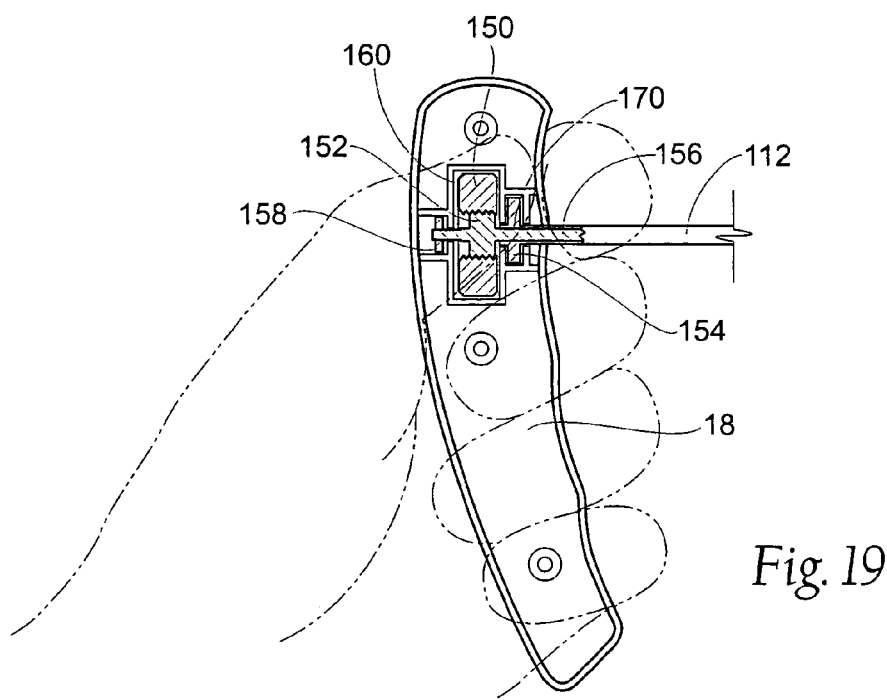
FIG. 19 is a sectional view of an actuator mechanism for deploying a cutting tip and showing placement of the tool in the user's hand.

The thumbwheel 150 extends, at least in part, from the handle 18 for manipulation by the thumb or index finger of the user, as seen in FIG. 19. The thumbwheel 150 desirably includes grooves or knurls for easy grasping and manipulation. While the thumbwheel 150 may be configured for manual manipulation, it is contemplated that the actuator may also be power-driven. The cap 152 is seated within the thumbwheel 150 and is desirably threaded or otherwise adapted to engage the wheel 150 so as to move with the wheel 150. The cap 152 is connected, e.g., by welding, to the plunger rod 156. The transmission ratio, and therefore the amount of torque delivered, may be controlled by altering the thread pitch of the cap 152.

Figure 21:
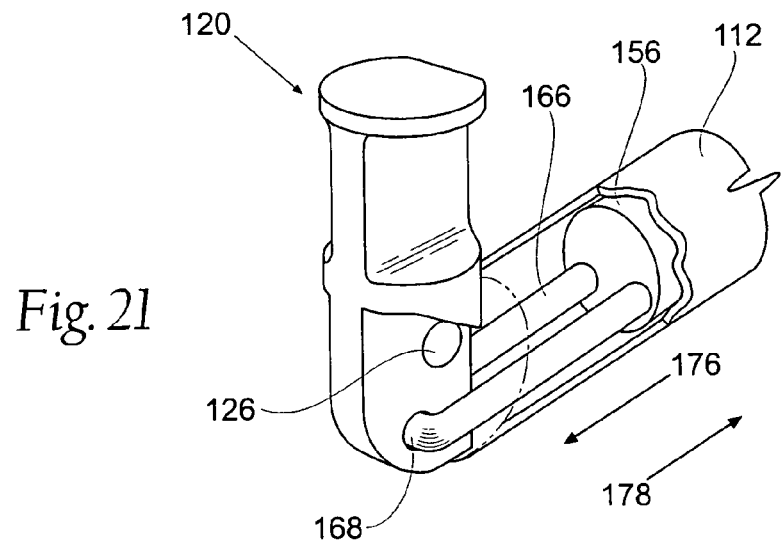
FIG. 21 is a cut-away view of the tether and hinge mechanism of the cutting tip.

The plunger rod 156 is sized and configured to be seated within the shaft 112 and to extend beyond the shaft 112 and thumbwheel 150 through bores in the cap 152 and thumbwheel 150. In the illustrated embodiment, the thumbwheel 150 and shaft 112 are positioned offset on the handle 18 for placement of the shaft 112 between the index and middle finger, as seen in FIG. 19. As shown in FIG. 21, the distal end of the plunger rod 156 is coupled to tether wire 166. The tether 160 is looped to pass through holes 168 in cutting tip 120 below pin 126 and is swaged or welded to the plunger rod 156. Movement of plunger rod 156 regulates pressure on the tether 160 to actuate the tip 120 between the deployed and non-deployed positions. The tether 160 will keep the tip 120 attached to shaft 112 in the event of breakage or failure of pin 126 to permit easy removal. This prevents parts from being left behind during removal, thereby providing an additional safety feature.

While the illustrated embodiment shows the tip 120 coupled to the shaft 112 and additionally tethered to the shaft 112 by a rod 156, it is contemplated that the tip 120 may be additionally tethered to the shaft 112 by any of a variety of ways to provide that the tip 120 remains tethered to the shaft 112 if the coupling element (e.g., pin 126) becomes inoperable. For example, in an alternative embodiment, the tip 120 is additionally tethered to shaft 112 by a cable or pulley (not shown).

The flange 154 is seated in a slot 170 within the handle 18 and is coupled to the shaft 112, e.g., by welding or by interference or compression fit. Desirably, the flange 154 includes an offset bore such that there is only one way in which it may be seated with slot 170. The flange 154 engages the shaft 112 within the handle 18 and is sized and configured to essentially prevent rotational movement of the shaft 112.

In the illustrated embodiment, the rod 156 has a rectangular end 172 sized and configured to pass through a complementary rectangular opening 174 in the stop 158. The stop 158 engages the rod 156 to prevent rotation of the rod 156 during actuation. The stop 158 is mounted to the plunger rod 156 and seated exterior to and against slot 160. The arrangement of the metal stop 158 against the plastic slot 160 creates additional frictional forces to provide additional strength and reinforcement and serves to limit the amount of torque delivered to the plunger rod 156.

Rotation of the thumbwheel 150 in a first direction advances the plunger rod 156 in a first direction along the shaft 112 to decrease tension on wire 166 and actuate deployment of the cutting tip 120. Rotation of the thumbwheel 150 in the opposite direction advances the plunger rod in the opposite direction within the shaft 112 and increases tension on wire 166 to actuate movement of the cutting tip 120 from the deployed to the non-deployed position. This arrangement converts the rotational movement of the thumbwheel 150 into the translational movement of the plunger rod 156.

Figure 22:
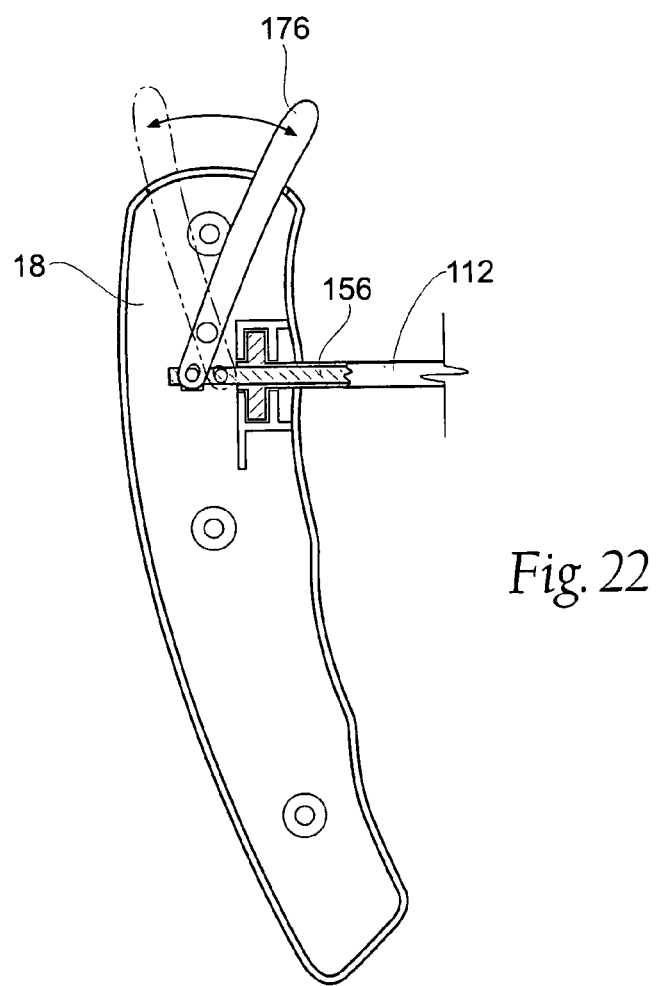
FIG. 22 is a side sectional view of an alternative embodiment of an actuator mechanism in which a lever actuates movement of the plunger rod.

In an alternative embodiment, shown in FIG. 22, a lever 176 is hingedly attached to the plunger rod 156. Movement of the lever 176 in a first direction advances the plunger in a first direction to deploy the cutting tip 120, and movement of the lever 176 in the opposite direction advances the plunger 156 in a second direction to move the cutting tip 120 from the deployed to the non-deployed position. In this manner, the lever 176 permits the physician to continuously and conveniently move the tip 120 itself without moving the shaft 112 to create a reciprocating cutting motion.

B. Gear Embodiment

Figure 20:
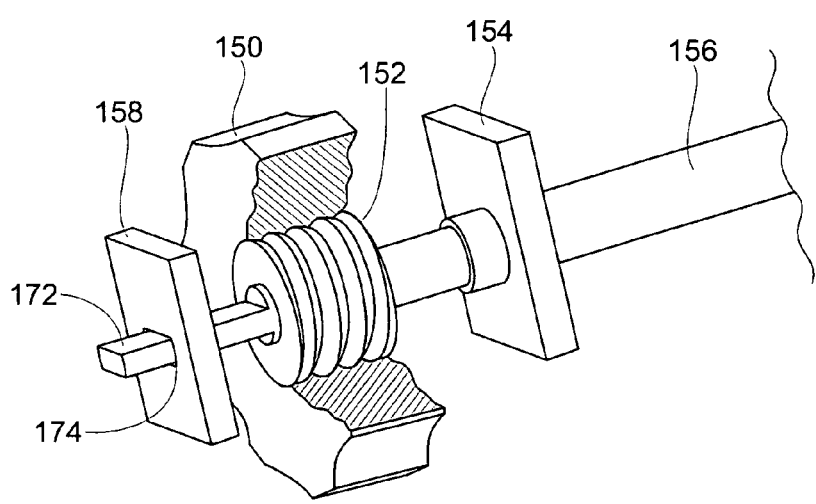
FIG. 20 is a close-up and partial sectional view of the thumbwheel, threaded cap, flange, and stop of FIG. 19.
Figure 23:
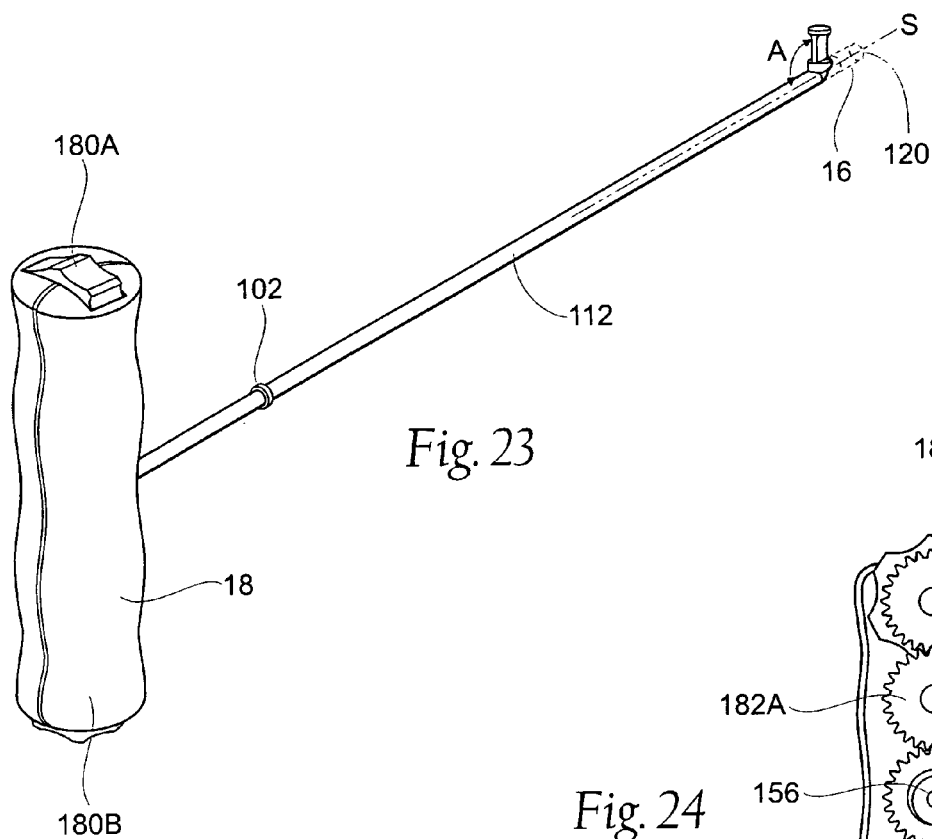
FIG. 23 is a perspective view of a tool incorporating an alternative embodiment of an actuator mechanism.
Figure 24:
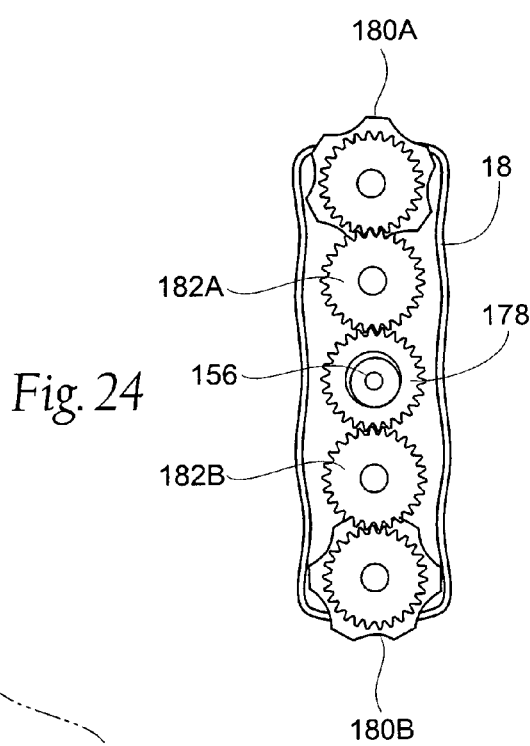
FIG. 24 is a top sectional view of an alternative embodiment of an actuator mechanism.
Figure 25:
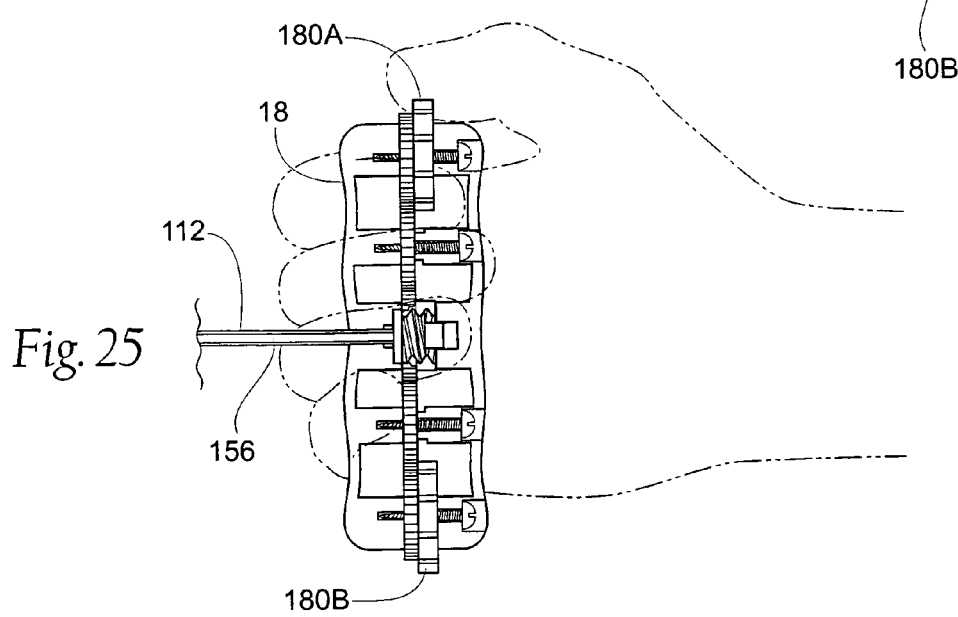
FIG. 25 is a side sectional view of an alternative embodiment of an actuator mechanism and showing placement of the tool in the user's hand.

FIGS. 23–25 illustrate an embodiment of an actuator similar to the embodiment of FIGS. 19–21. The actuator provides a series of gears that interact to convert rotational motion to translational motion.

A central gear 178 is similar in configuration and function to the thumbwheel 150 shown in FIGS. 19–21. The central gear 178 and shaft 112 are centered along the bottom of the handle 18 for placement of the shaft 112 between the middle and ring fingers.

Control knobs 180A and 180B are provided at each end of the handle 18 for actuation by the user's thumb. Alternatively, the control knobs 180A and 180B may be driven by a motor. Each control knob 180A and 180B defines a gear that actuates a corresponding intermediate gear 182A or 182B positioned between the control knob 180A or 180B and the central gear 178. Rotation of the control knob 180A or 180B actuates the corresponding intermediate gear 182A or 182B and the central gear 178. Rotational movement of the control knob 180 is thereby converted into translational movement of the plunger rod 156, similar to the previous embodiment.

The symmetric design is designed for easy use by either the right or left hand. Further, the symmetric design allows easy rotation of the handle 18.

In use, the shaft 112 is advanced through a cannula 104. The cutting tip 120 is extended beyond the distal end of the cannula 104. A control knob 180A or 180B is rotated to deploy the cutting tip 130 to the desired angle. The physician then creates a desired void by performing a series of translational and rotational movements of the shaft 112. The physician then returns the cutting tip 120 to the non-deployed position.

If desired, the handle 18 can then be rotated 180°. The opposing control knob 180A or 180B is then manipulated to again deploy the cutting tip 120 to a desired angle and another series of translational and rotational movements may be performed.

Once the desired void is created, the physician returns the tip 120 to the non-deployed position. The tool 100 is withdrawn from the patient. The physician then completes the procedure by filling the void with a bone cement or bone substitute, removing the cannula 104, and closing the incision.

The rate and/or force of cutting may be controlled by altering the transmission ratio. The force may be varied by varying the screw thread pitch or the transmission gear ratio. The rate of motion (i.e., speed of actuation) may be varied by manually or mechanically varying the speed of actuation.

III. Alternative Embodiments of Mechanical Void Creators

A. Shape Memory Alloys

Figure 26:
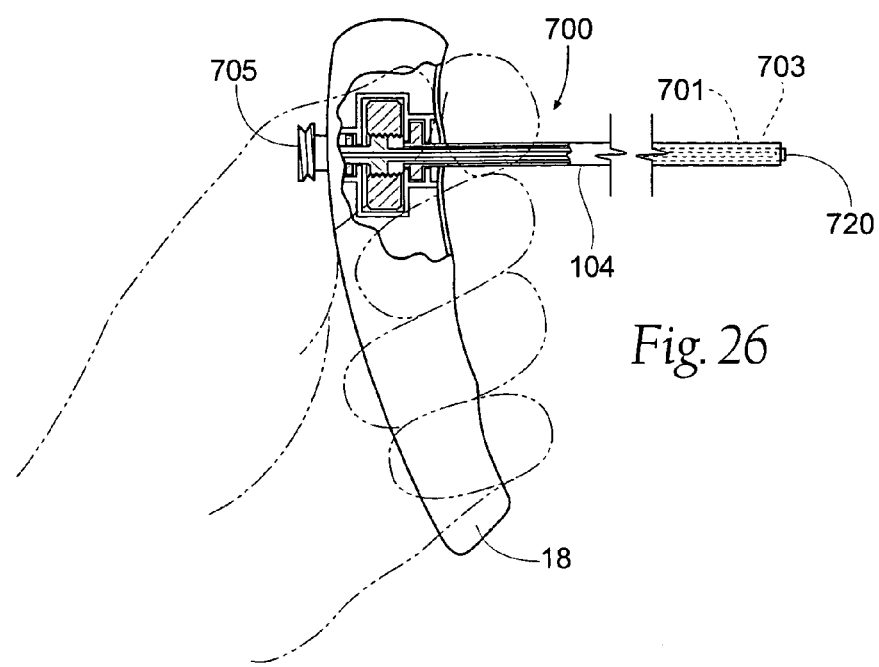
FIG. 26 is a side partial section view illustrating an alternative embodiment of a mechanical bone cutting tool illustrating the cutting tip in a straightened or malleable state and retracted within a cannula.
Figure 27:
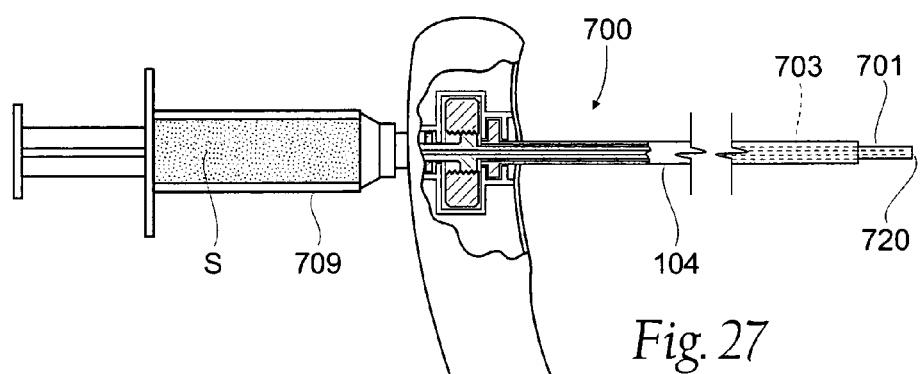
FIG. 27 is a view similar to FIG. 26 and illustrating advancement of the cutting tip beyond the distal tip of the cannula and the introduction of fluid to activate the cutting tip.
Figure 28:
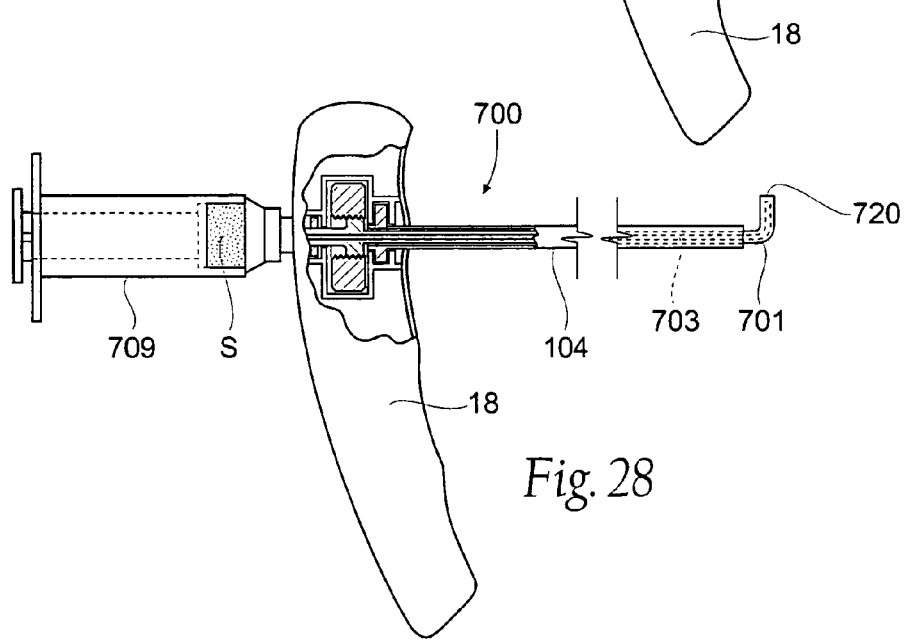
FIG. 28 is a view similar to FIG. 27 and illustrating activation of the cutting tip to a predetermined configuration.

FIGS. 26–28 illustrate an embodiment of a tool 700 employing a cutting tip 720 formed of a shape memory alloy. Use of a shape memory alloy allows for a smaller instrument as the hinge mechanism is no longer needed to activate the tip. Smaller instruments are safer and can access smaller vertebral bodies located higher in the spine. Smaller instruments are also less invasive and are less traumatic to the patient, allowing for a faster recuperation time.

A malleable rod 701 formed of a shape memory alloy, e.g., Nitinol, is provided. It is contemplated that the rod 701 may be of a variety of different diameters, tip configurations, and actuation angles. The rod 701 has a malleable or straightened state (FIGS. 26 and 27) and an activated or articulated predetermined, desired state (FIG. 28). The rod 701 is sized and configured for passage in a straightened or malleable state through a cannula 104 into a vertebra or any bone surface. Once inserted into the bone, the rod 701 returns to its predetermined, desired memory shape as a result of either the body temperature of the patient or by means of an electrical impulse (e.g., cooling, heat, voltage, etc.). For example, the distal end of the rod 701 is activated to an angle, e.g., 90°, to form an elbow defining a cutting tip, as shown in FIG. 28. In a representative embodiment, the length from the distal end of the rod to the bend is approximately 0.5 cm. Cutting of the bone is accomplished by a rotating motion or a push-pull motion or a combination of both motions, as previously described. The rod 701 desirably includes a lumen 703 that permits introduction of a cooling or heating media (S), e.g., saline, to return the rod 701 to a straightened state allowing for easy withdrawal.

Figure 35A:
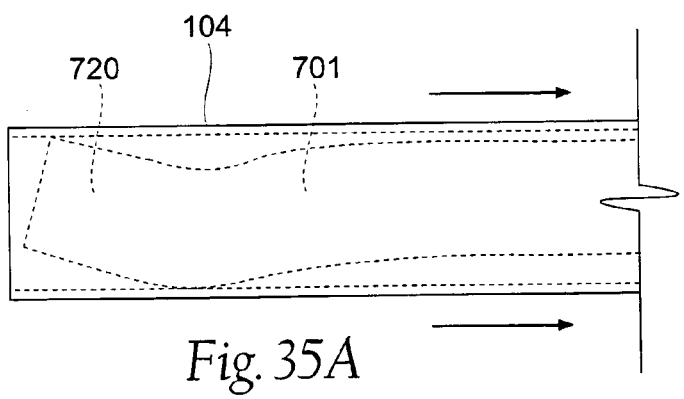
FIG. 35A is a side view illustrating a pre-bent or formed cutting tip confined by a cannula.
Figure 35B:
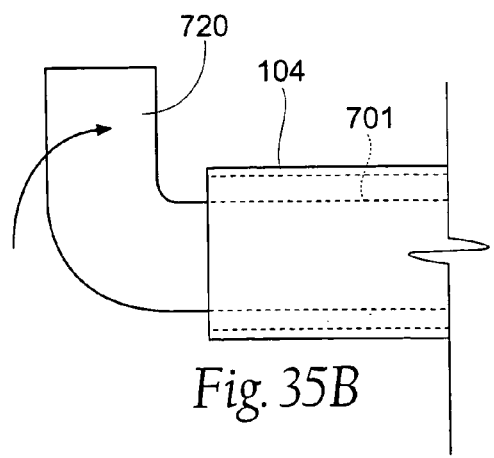
FIG. 35B is a side view similar to FIG. 35A illustrating the deployment of the pre-bent or formed cutting tip by extension of the tip beyond the cannula.

In another embodiment, the rod 701 is formed from a shape memory alloy with an activation temperature that is equal to room temperature, i.e., the rod 701 is fully austenitic at room temperature. Therefore, the rod 701 is fully articulated to its predetermined shape at room temperature. The rod 701 is chilled to a martensitic condition (malleable state) prior to insertion into bone, allowing for easy insertion. The rod 701 articulates to the predetermined, desired position upon returning to room temperature. This ensures that the proximal end of the cutting tip 720 attains full activation without depending on heat transfer from the distal end of the rod 701 (which is in contact with the patient) or any outside means (e.g., heat, voltage, etc.). A lumen 703 is provided in the rod 701 to facilitate the introduction of a cooling media (S), e.g., chilled saline, to deactivate the material and allow for easy withdrawal. In another alternative embodiment, the alloy is super-elastic and the cannula 104 confines the pre-bent or formed cutting tip 720 until the activation mechanism deploys the cutting tip 720 to extend beyond the cannula 104 (see FIGS. 35A and 35B).

In another alternative embodiment, the rod 701 may be used to straighten the cannula 104 which is formed of a shape memory alloy. In this embodiment, the cutting tip 720 is disposed on the shape memory cannula 104 (not shown). The cannula 104 is educated to have a curved tip the rod 701 is moveably disposed within the cannula 104 to straighten the cannula 104 by fully engaging the rod 701 within the cannula 104 (i.e. by pushing the rod 701) and to allow the cannula 104 and cutting tip 720 to curve or articulate by pulling back on the rod 701. Desirably, the rod 701 is made of a rigid material, such as stainless steel.

In another embodiment, the activation temperature of the alloy is set at a temperature higher than body temperature. In this embodiment, the rod 701 is malleable for insertion and withdrawal. The rod 701 achieves full activation to its predetermined shape only through the application of heat or voltage. This permits control of the change of the state of the rod 701 from malleable to the predetermined shape, or any percentage there between, using a potentiometer or other suitable device.

The rod 701 may be attached to a handle by a standard square drive or Hudson-style orthopedic fitting on the proximal end (not shown). A torque-regulating handle could be mated to the rod 701 to allow for torque-limiting rotational scraping.

In one embodiment, the rod 701 is fixedly attached or otherwise coupled to a handle 18 having an actuator mechanism. For example, in the illustrated embodiment, the rod 701 is coupled to a thumbscrew 152 and is driven by an actuator mechanism similar to the mechanism illustrated in FIGS. 19 and 20. The rod 701 is actuated (moved in fore and aft directions) within the cannula 104 by the actuator mechanism. This permits the cutting tip 720 to be retracted (FIG. 26) in a malleable state within the cannula 104 for easy insertion and withdrawal and then extended (FIG. 27) beyond the distal end of the cannula 104 within bone and activated for use (FIG. 28).

In a preferred embodiment, the handle 18 includes a luer fitting 705. The fitting 705 is sized and configured to mate with a complementary luer fitting 707 on a fluid introduction device, e.g., a syringe 709, to establish fluid communication between the lumen 703 and the fluid introduction device 709. Fluid, e.g., chilled or heated saline, may be introduced from the syringe 709 through the rod lumen 703 to control movement of the rod 701 between the malleable (deactivated) and activated states.

Figure 29:
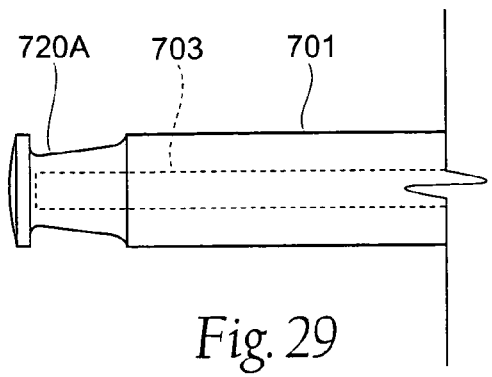
FIG. 29 is a side view of an alternative embodiment of a cutting tip illustrating the cutting tip in a straightened or malleable state.
Figure 30:
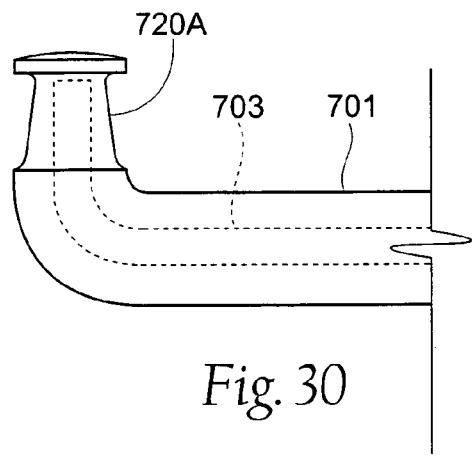
FIG. 30 is a view similar to FIG. 29 illustrating the cutting tip in the activated state.

In an alternative embodiment, shown in FIGS. 29 and 30, a cutting tip 720A of a desired configuration is formed at the distal end of the malleable rod 701. The tip 720A may be a separate piece welded to the rod 701, or the tip 720A may be carved or otherwise formed in the rod 701, e.g., by conventional machining techniques. In the illustrated embodiment, the cutting tip 720A is of a conical trunk and domed disc configuration similar to the embodiment illustrated in FIGS. 17 and 18. It is apparent, however, that the configuration of the cutting tip 720A can be varied according to the procedure being performed and/or to accommodate individual anatomy. In one embodiment, the entire rod 701, including the cutting tip 720A, are formed of the shape memory alloy. The rod 701 yields from a malleable state (FIG. 29) to the activated state (FIG. 30) as previously described. The rod 701 desirably includes a lumen 703 to permit introduction of a fluid media to control movement between the deactivated and activated states, as also previously described.

Figure 31:
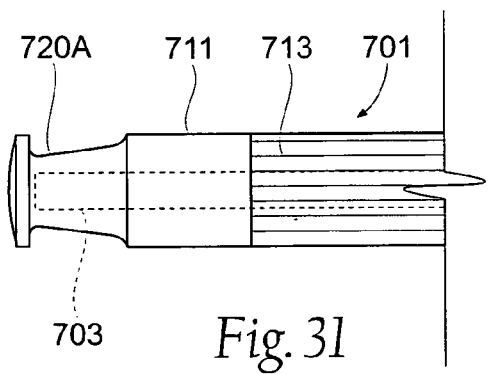
FIG. 31 is a side view of an alternative embodiment of a cutting tip illustrating the cutting tip in a straightened or malleable state.
Figure 32:
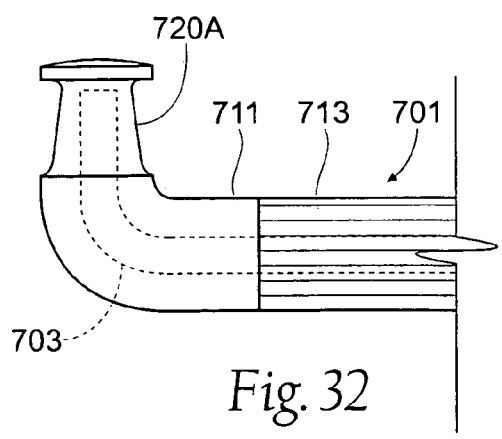
FIG. 32 is a view similar to FIG. 31 illustrating the cutting tip in the activated state.
Figure 33:
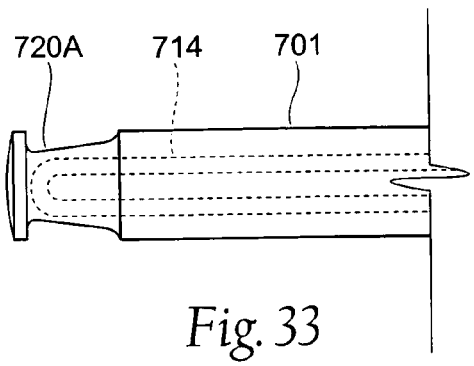
FIG. 33 is a side view of an alternative embodiment of a cutting tip carried by a shaft and illustrating a dual lumen extending through the shaft into the cutting tip.
Figure 34:
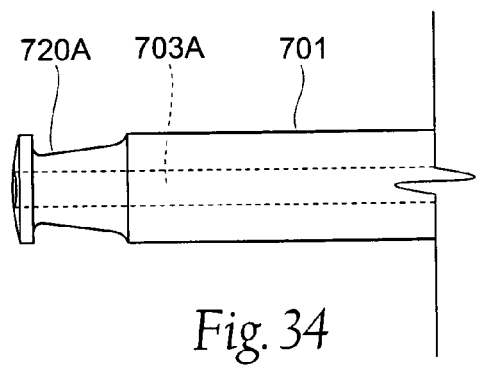
FIG. 34 is a side view of an alternative embodiment of a cutting tip illustrating a throughbore extending through the cutting tip.

In an alternative embodiment, illustrated in FIGS. 31 and 32, the tip 720A and a distal portion 711 of the rod 701 are formed of a shape memory alloy. A rod body 713 is formed of any suitable biocompatible, surgical grade material. The distal portion 711, carrying the cutting tip 720A, is welded or otherwise fixed to the rod body 713. The distal portion 711 of the rod 701 yields from a malleable state (FIG. 31) to the activated state (FIG. 32). The rod 701 desirably includes a lumen 703 to permit introduction of a fluid media to control movement between the deactivated and activated states. In an alternative embodiment, the rod 701 may include a dual lumen 714 so that fluid media can circulate through the shaft 112 and desirably through the cutting tip 720 (see FIG. 33) In another alternative embodiment, the rod 701 may include a throughbore 703A to accommodate more thermal flow (see FIG. 34).

B. Alternative Mechanical Void Creators

Figure 36:
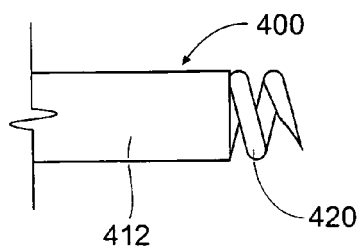
FIG. 36 is a side view of an alternative embodiment of a mechanical void-creating device.

FIG. 36 shows an alternative embodiment of a mechanical tool 400 for creating a void in an interior body region. A shaft 412 carries a sharp, stout, metal spring 420 on the end of a shaft 412. The shaft 412 can be rotated against the direction of the spring 420 causing it to cut bone (or other tissue) in an expanding fashion. The tool 400 is sized and configured to be introduced through a cannula (not shown) with the spring 420 extending beyond the cannula and the shaft 412 rotated into the tissue a short distance at a time. The shaft 412 can then be withdrawn to remove any captured tissue. If no tissue is captured, the tool 400 is reintroduced farther into the tissue and tissue removal is again attempted. The tool 400 may also be used to loosen tissue to allow better cutting and/or removal by other mechanical tools.

Figure 37:
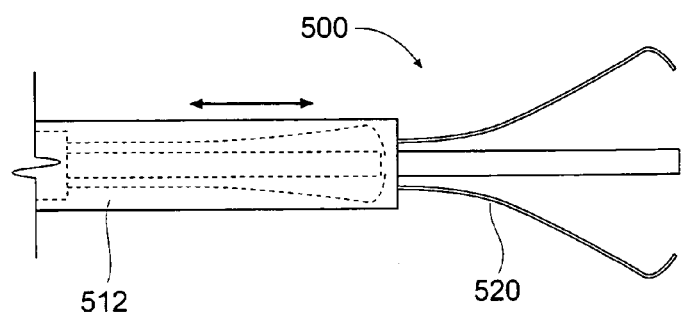
FIG. 37 is a side view of an alternative embodiment of a mechanical void-creating device.

FIG. 37 shows another embodiment of a mechanical tool 500 for creating a void in an interior body region. Two or more fingers 520 are carried on the distal end of a shaft 512. Preferably, the shaft 512 carries four fingers 520, two fingers 520 facing each other. The fingers 520 are introduced into the tissue through a cannula (not shown), and then mechanically closed with a pulley-type system or other similar system to grab tissue for extraction. Desirably, the fingers 520 are adapted to further expand as the size of the void increases. It is apparent that the length of the fingers 520 may be chosen to suit the intended use and particular individual anatomy.

Figure 38:
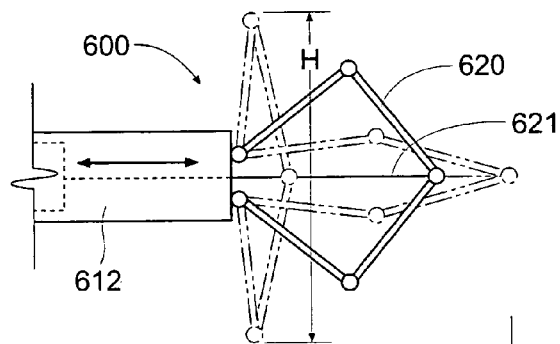
FIG. 38 is a side view of an alternative embodiment of a mechanical void-creating device.
Figure 39:
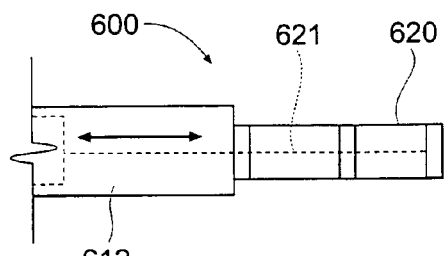
FIG. 39 is a top view of the device shown in FIG. 38.

FIGS. 38 and 39 show another embodiment of a mechanical tool 600 for creating a void in an interior body region. The tool includes a hinged void-creating device 620 carried on the distal end of the shaft 612. The void-creating device 620 may be used to create a void or to loosen tissue to allow better cutting and removal by other mechanical tools.

The void-creating device 620 provides for adjusting the height of the device 620. A positioning rod 621 is coupled to the device 620 for expanding and contracting the device 620. The height may be adjusted by drawing in the rod 621 to increase the height H and pushing out on the rod to decrease the height H of the device 620. Calibrated markings (not shown) may be provided on the rod handle to indicate the dimension of the device 620 as the rod 621 is drawn back or advanced. The height H may also be chosen to suit the intended use and particular individual anatomy.

Figure 40:
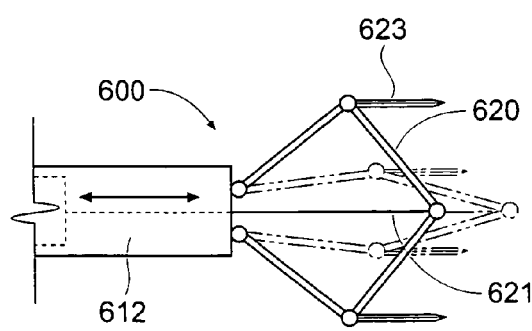
FIG. 40 is a side view of an alternative embodiment of the device of FIGS. 38 and 39 in which spring blades extend from the device.

FIG. 40 shows an embodiment similar to FIGS. 35 and 36, but additionally providing a spring blade or series of spring blades 623 for more aggressive cutting. The spring blades 623 are coupled to the last blades out of the cannula and desirably pre-bent to cut parallel to the end plates.

IV. Creation of Voids in Bone

Two or more different mechanical cutting tools of the type described may also be used in combination to form a cavity or void of a desired size and configuration in a targeted bone. In addition, one or more mechanical cutting tools may be used in combination with one or more expandable void-creating tools to form the desired void.

Expandable structures for creating voids in bones are described in U.S. Pat. Nos. 4,969,888, 5,827,289, 5,972,015, 6,235,043, 6,248,110, and 6,607,544, all of which are herein incorporated by reference.

Fracture reduction and deformity correction is influenced by a variety of factors, including, but not limited to, acuteness of the fracture, bone quality (e.g. osteoporosis, bone cancers, steroid-induced osteoporosis), and healing. In some fractures, expansion of the expandable structure may be distorted by a region or regions of hard bone. This results in a high pressure within the expandable structure and low volume of expansion media within the expandable structure. The use of a mechanical cutting tool to selectively break up the region of hard bone will allow the expandable structure to achieve a more consistent and reliable fracture reduction. Mechanical cutting or scraping tools will break bone, but an expandable structure is required for the en-masse endplate reduction and deformity correction.

In use, an access path to bone is made using a conventional access cannula by techniques commonly known in the art. A first void creator, which may be a mechanical cutting tool or an expandable structure, is then introduced into a bone to create a void. The first void creator is then removed. A second void creator, which may be the same as or different from the first void creator, is then inserted into the bone to enlarge or further define the void to form a void of a desired size and configuration. The second void creator is then removed. If desired, a third void creator, which may be the same or different from the first and/or second void creators, may then be introduced to further enlarge and define the void and then removed. Desirably, a filling material, e.g., bone cement or bone substitute, is then injected or otherwise introduced into the void to fill the void.

Figure 41A:
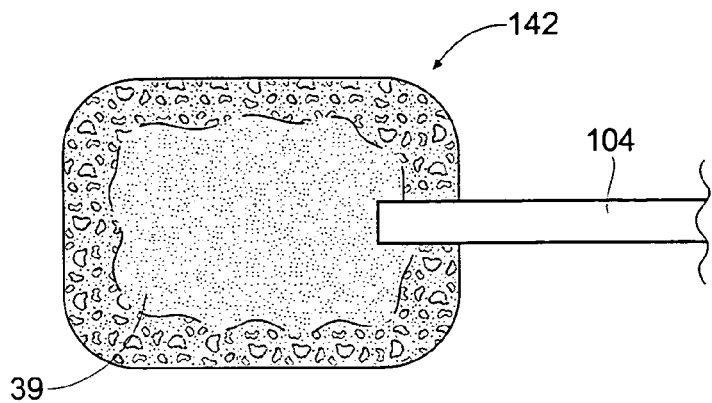
FIGS. 41A–D illustrate a method of creating and filling a void in bone in which a first mechanical cutting tool is used to create a void in bone and a second mechanical cutting tool is used to expand and/or further define the void.
Figure 41B:
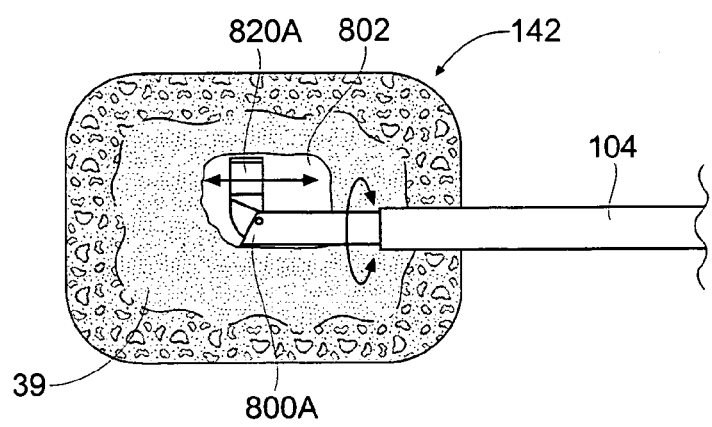
Figure 41C:
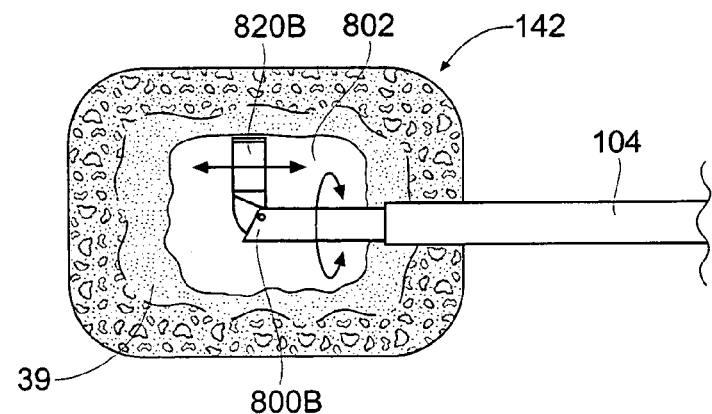
Figure 41D:
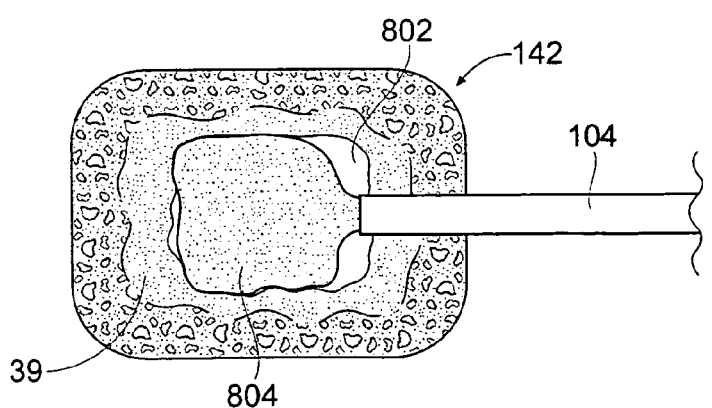
Figure 42A:
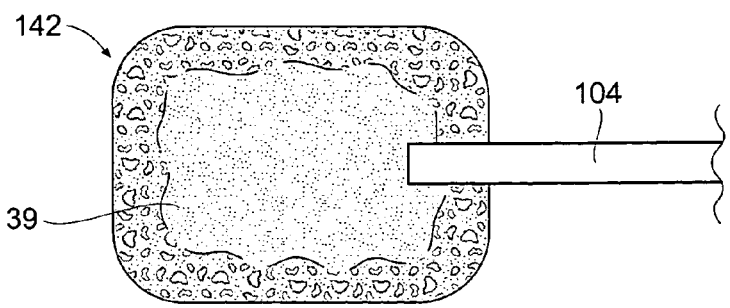
FIGS. 42A–E illustrate an alternative method of creating and filling a void in bone in which a first mechanical cutting tool is used to create a void in bone and a second mechanical cutting tool and then an expandable body are used to expand and/or further define the void.
Figure 42B:
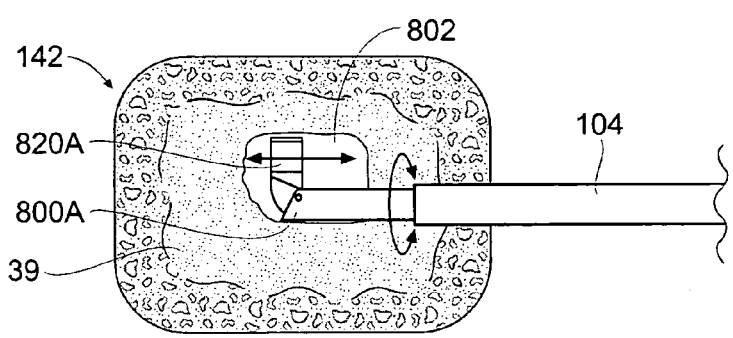
Figure 42C:
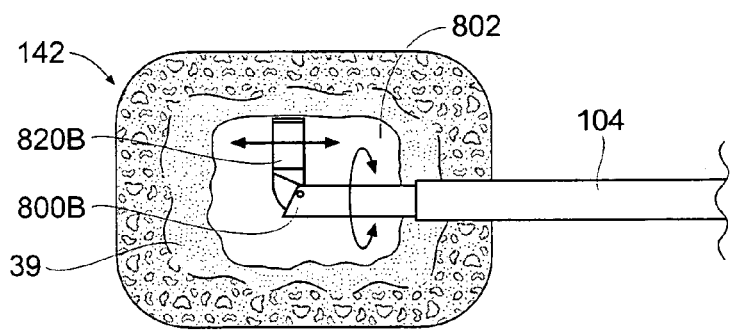
Figure 42D:
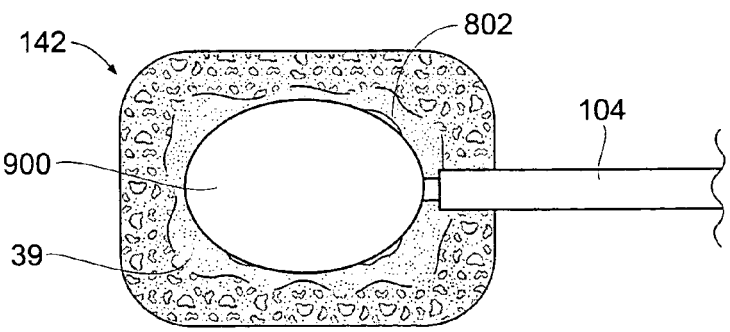
Figure 42E:
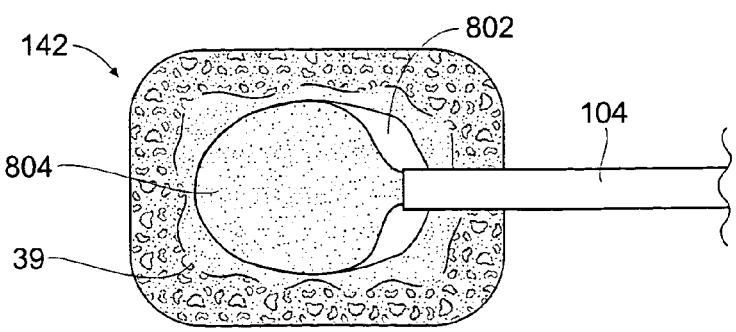

In one embodiment, illustrated in FIGS. 41A–41D, a first mechanical cutting tool 800A and a second mechanical cutting tool 800B, which may be different in size and/or configuration from the first cutting tool 800A, are used to create a void 802 of a desired size and configuration. An access cannula 104 is percutaneously introduced to provide an access path into a bone, e.g., a vertebra 142 (FIG. 41A). The first mechanical cutting tool 800A is introduced through the cannula 104 into the cancellous bone 39 of the vertebra 142. The cutting tip 820A is manipulated in a series of longitudinal and/or rotational movements to create a void 802 in the cancellous bone 39 (FIG. 41B). The first cutting tool 800A is then removed. The second mechanical cutting tool 800B is then introduced and manipulated in a series of longitudinal and/or rotational movements (FIG. 41C). The second cutting tool 800B desirably has a cutting tip 820B of a different size and/or configuration to enlarge and/or otherwise further define the void 802 created by the first tool 800A. For example, in the illustrated embodiment, the second cutting tool 800B has a cutting tip 820B of a greater height than the first cutting tip 820A to enlarge the void 802, but is of a similar configuration. The second cutting tool 800B is then removed. A filler material 804, e.g., bone cement or bone substitute, may then be introduced into the void 802 to fill the void 802 (FIG. 41D).

Alternatively, as shown in FIGS. 42A–42E, after removal of the second cutting tool 800B, an expandable structure 900 may be introduced through the cannula 104 and expanded to enlarge and/or further define the void 802 created by the first and second mechanical cutting tools 802A and 802B. While in the illustrated embodiment the expandable structure 900 takes the form of a balloon adapted to expand or form a void by compression of cancellous bone, the expandable structure 900 may be any suitable device which can be expanded to enlarge and/or further define the void. For example, the expandable structure 900 may also be a mechanical jack, retractor, or spring. Desirably, the expandable structure 900 has a collapsed condition permitting insertion of the expandable structure 900 through the cannula 104 and an expanded condition in which the expandable structure 900 compacts cancellous bone 39 upon expansion within the cancellous bone 39. The expandable structure 900 is then removed. The void 802 may then be filled, as previously described.

Figure 43A:
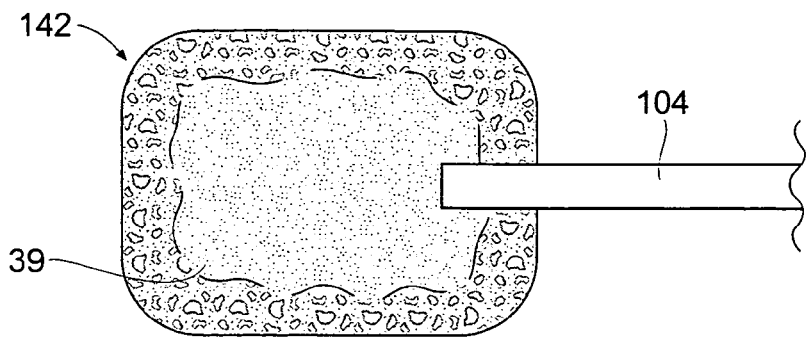
FIGS. 43A–D illustrate an alternative method of creating and filling a void in bone in which a first expandable body is used to create a void in bone and a second expandable body is used to expand and/or further define the void.
Figure 43B:
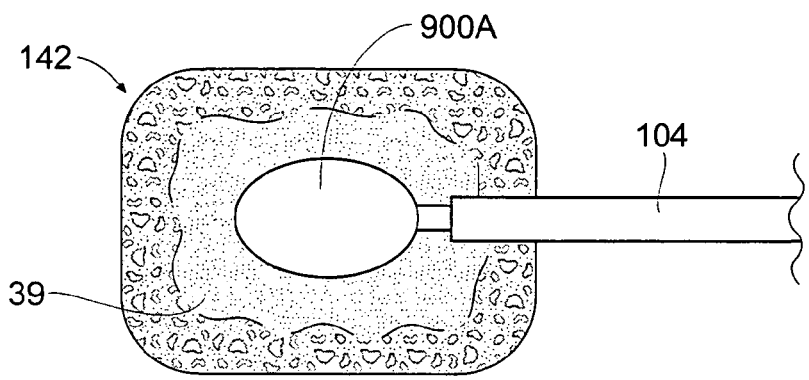
Figure 43C:
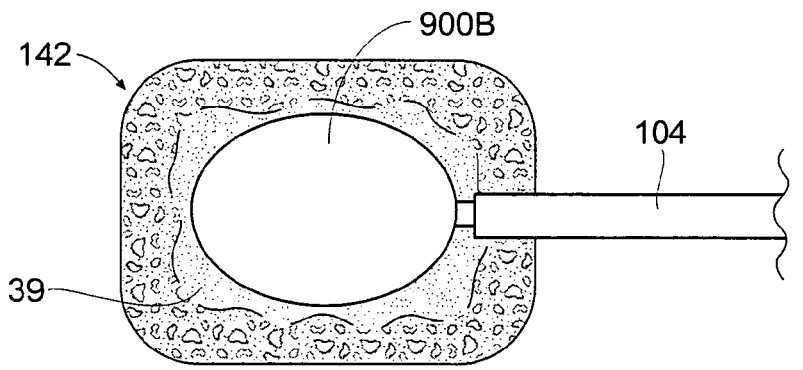
Figure 43D:
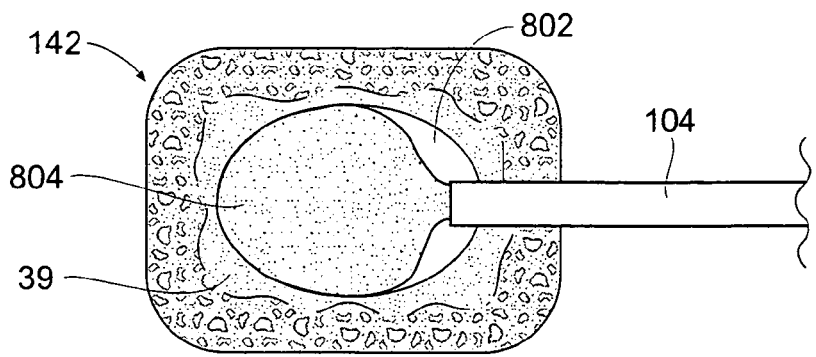
Figure 44A:
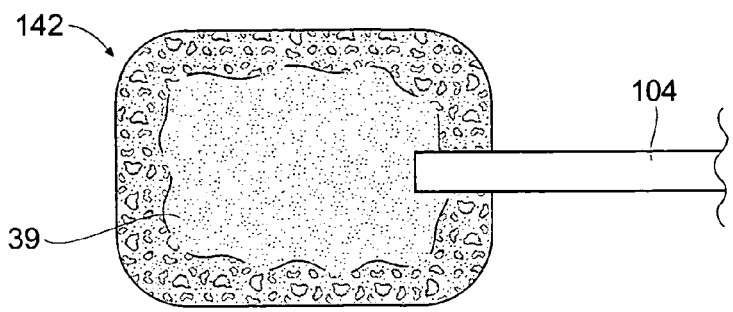
FIGS. 44A–E illustrate an alternative method of creating and filling a void in bone in which a first expandable body is used to create a void in bone and a second expandable body and then a mechanical cutting tool are used to expand and/or further define the void.
Figure 44B:
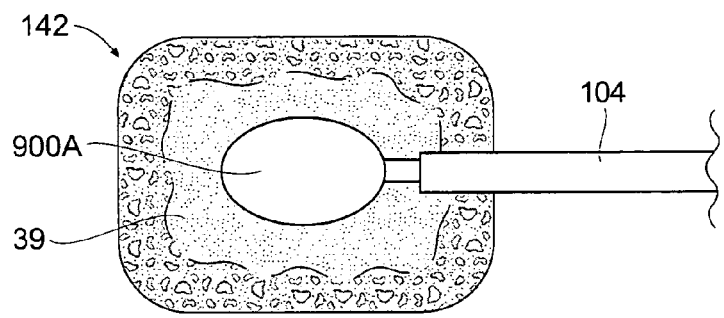
Figure 44C:
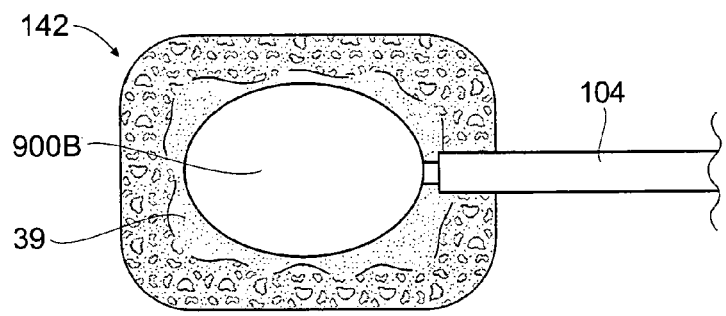
Figure 44D:
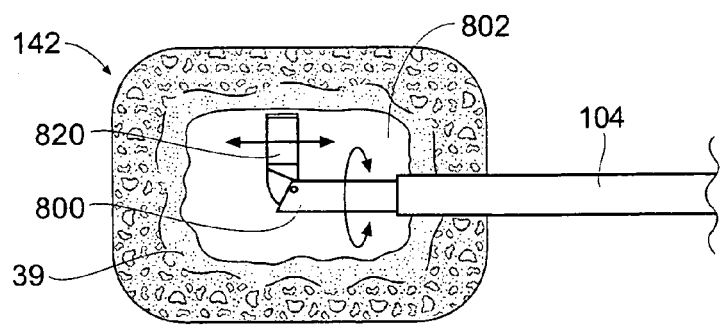
Figure 44E:
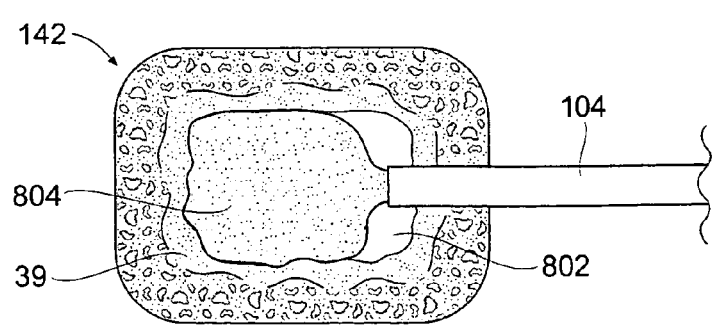

In another embodiment, illustrated in FIGS. 43A–43D, a first expandable structure 900A and a second expandable structure 900B, which may be different in size and/or configuration from the first expandable structure 900A, are used to create a void 802 of a desired size and configuration. An access cannula 104 is percutaneously introduced to provide an access path into a vertebra 142 (FIG. 43A). The first expandable structure 900A is introduced through the cannula 104 in the collapsed condition into the cancellous bone 39 of the vertebra 142. The expandable structure 900A is then expanded to create a void 802 in cancellous bone 39 (FIG. 43B). The first expandable structure 900A is then removed. The second expandable structure 900B is then introduced and expanded (FIG. 43C). The second expandable structure 900B is desirably of a different size and/or configuration such that expansion of the second expandable structure 900B enlarges and/or otherwise further defines the void 802 created by the first expandable structure 900A. For example, in the illustrated embodiment, the second expandable structure 900B is of a larger volume, but is of a similar configuration. It is contemplated, however, that the second expandable structure 900B may be of a different configuration than the first expandable structure 900A. The second expandable structure 900B is then removed. A filler material 804, e.g., bone cement or bone substitute, may then be introduced into the void 802 to fill the void 802 (FIG. 43D).

Alternatively, as shown in FIGS. 44A–44E, after removal of the second expandable structure 900B, if desired, a mechanical cutting tool 800 may be introduced through the cannula 104 to enlarge and/or further define the void 802 created by the first and second expandable structures 900A and 900B. The cutting tool 800 is then removed. The void 802 may then be filled, as previously described.

Figure 45A:
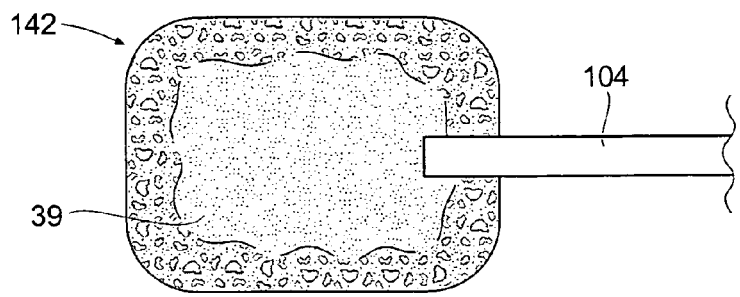
FIGS. 45A–E illustrate an alternative method of creating and filling a void in bone in which a first expandable body is used to create a void in bone and a mechanical cutting tool and then a second expandable body are used to expand and/or further define the void.
Figure 45B:
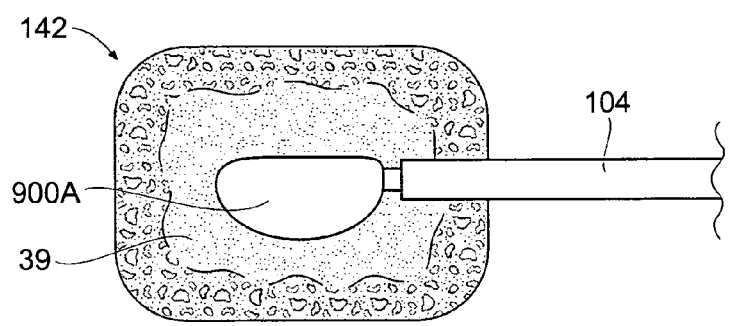

FIGS. 45A–45E illustrate another method of creating a void 802 in bone of a desired size and configuration. An access cannula 104 is percutaneously introduced to provide an access path into a vertebra 142 (FIG. 45A). A first expandable structure 900A is introduced through the cannula 104 in the collapsed condition into the cancellous bone 39 of the vertebra 142. The expandable structure 900A is then expanded to create a void 802 in cancellous bone 39 (FIG. 45B) Because the reticulum of the cancellous bone 39 may be somewhat dense, it may be difficult for the expandable structure 900A to sufficiently compact the cancellous bone 39 to permit full expansion of the expandable body 900A. This may occur with older fractures or in normal bone that has been injured by trauma, but is not necessarily osteoporotic. In this case, the expandable structure 900A may expand preferentially in a given direction depending on the density of the reticulum, but is not able to expand to its full preformed shape, as seen in FIG. 45B. The first expandable structure 900A is then removed.

Figure 45C:
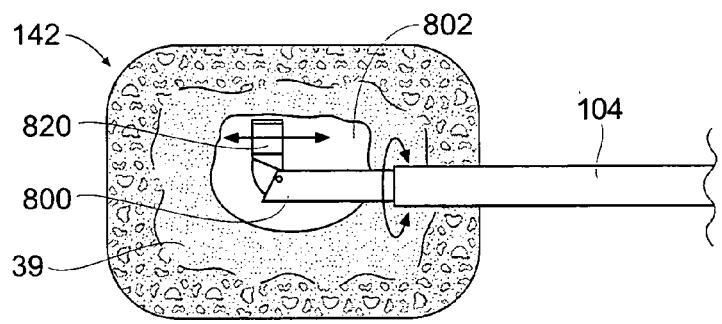

A mechanical cutting tool 800 is then introduced (FIG. 45C). The cutting tip 820 is manipulated in a series of longitudinal and/or rotational movements to enlarge and/or otherwise further define the void 802 created by the expandable structure 900A. The cutting tool 800 is then removed.

Figure 45D:
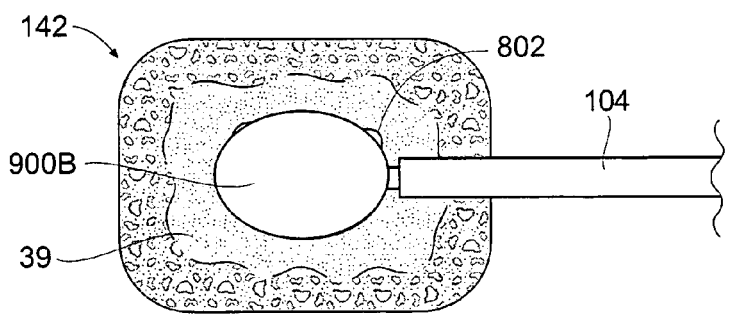
Figure 45E:
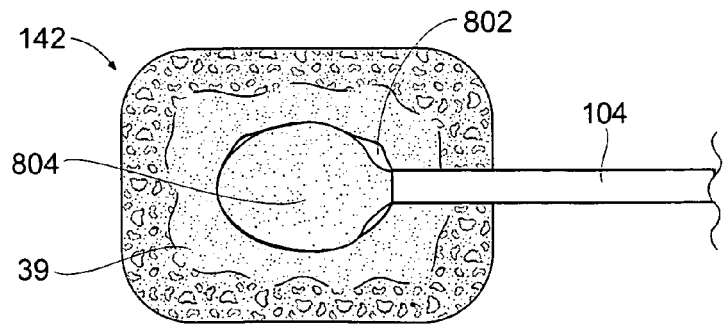

If desired, a second expandable structure 900B, which may be of a different size and/or configuration from the first expandable structure 900A, is then introduced prior to filling the void 802 (FIG. 45D). Use of the cutting tool 800 to break or cut the reticulum and expand the void 802 allows the second expandable structure 900A to fully expand. The second expandable structure 900A is then expanded to enlarge and/or otherwise further define the previously created void 802. The second expandable structure 900B is then removed. Alternatively, instead of a second expandable structure 900B, the first expandable structure 900A may be reintroduced, re-expanded, and then removed. A filler material 804 may then be introduced into the void 802 to fill the void (FIG. 45E).

Figure 46A:
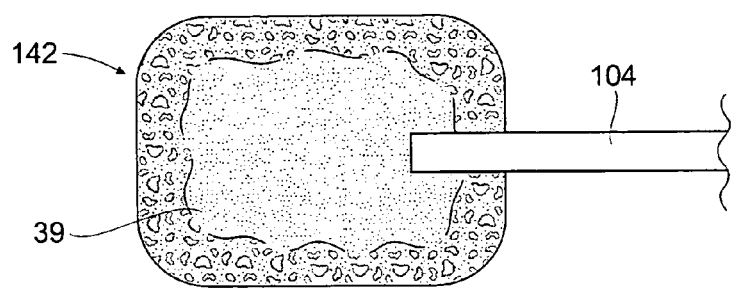
FIGS. 46A–E illustrate an alternative method of creating and filling a void in bone in which an expandable body is used to create a void in bone and a first mechanical cutting tool and then a second mechanical cutting tool are used to expand and/or further define the void.
Figure 46B:
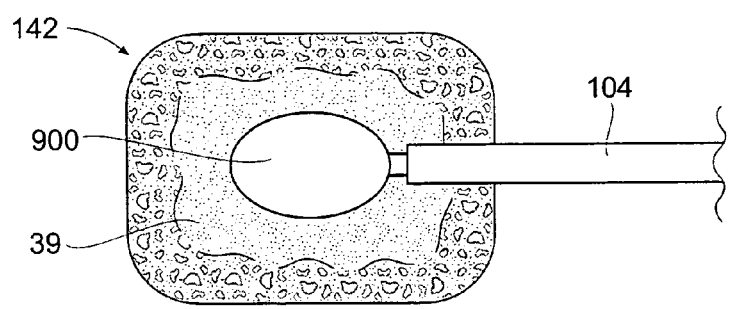

In an alternative method shown in FIGS. 46A–46E, an access cannula 104 is percutaneously introduced to provide an access path into a vertebra 104 (FIG. 46A). An expandable structure 900 is introduced and expanded to create a void 802 in cancellous bone 39 (FIG. 46B) The first expandable structure 900A is then removed.

Figure 46C:
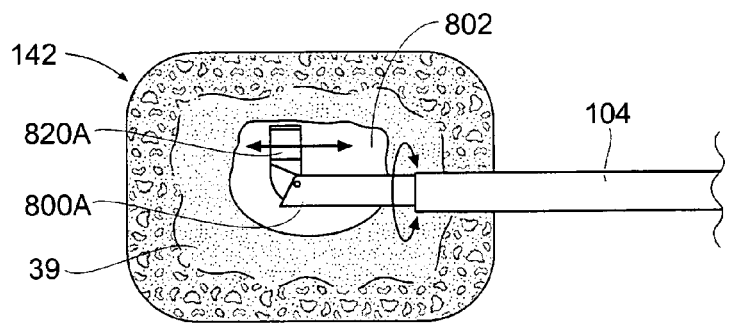

A first mechanical cutting tool 800A is then introduced (FIG. 46C). The cutting tip 820A is manipulated in a series of longitudinal and/or rotational movements to enlarge and/or otherwise further define the void 802 created by the expandable structure 900. The cutting tool 800 is then removed.

Figure 46D:
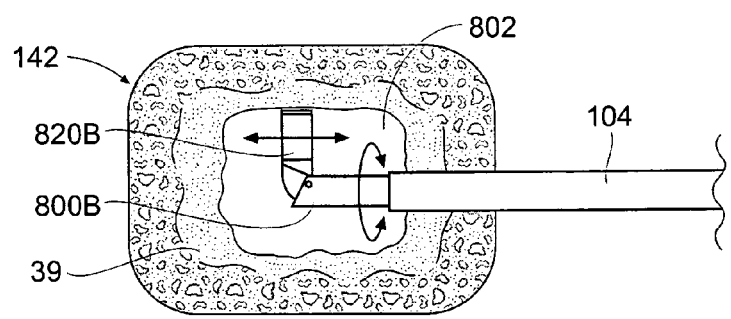
Figure 46E:
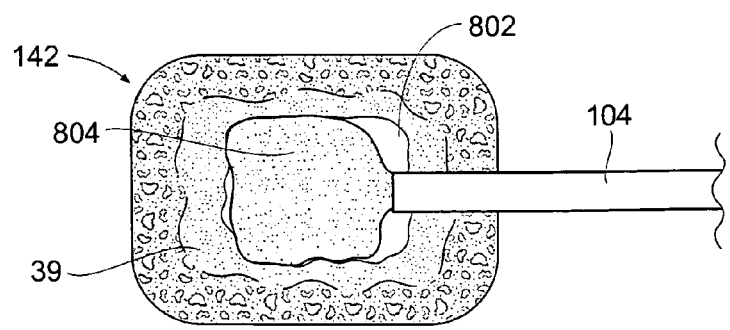
Figure 47A:
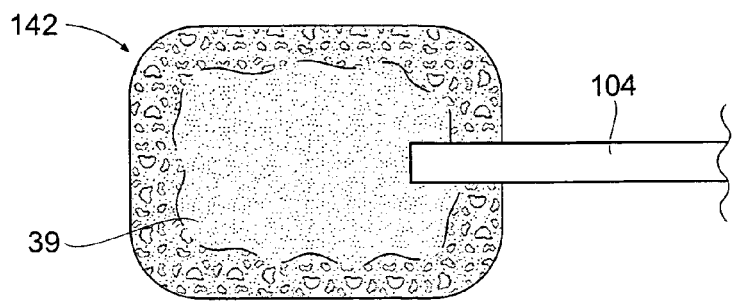
FIGS. 47A–E illustrate an alternative method of creating and filling a void in bone in which a first cutting tool is used to create a void in bone and an expandable body and then a second mechanical cutting tool are used to expand and/or further define the void.
Figure 47B:
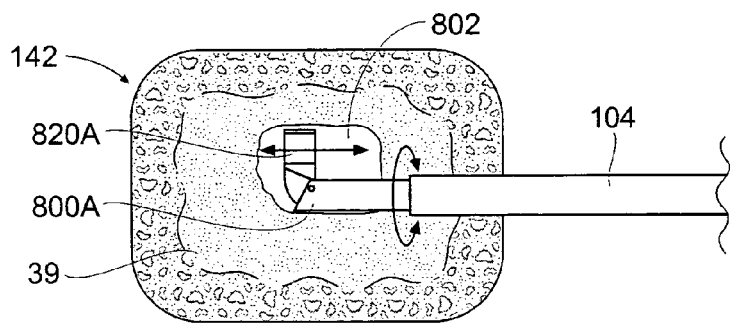
Figure 47C:
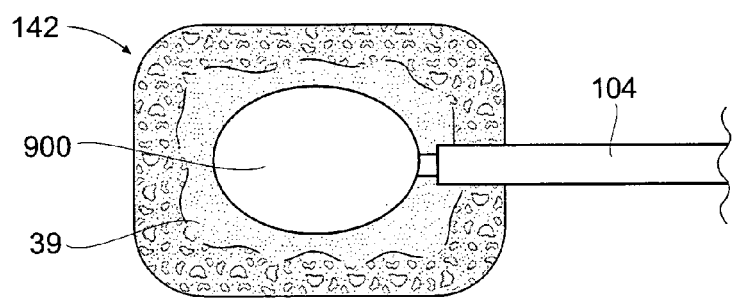
Figure 47D:
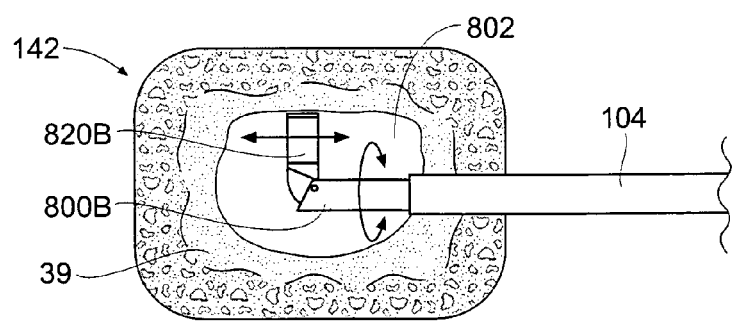
Figure 47E:
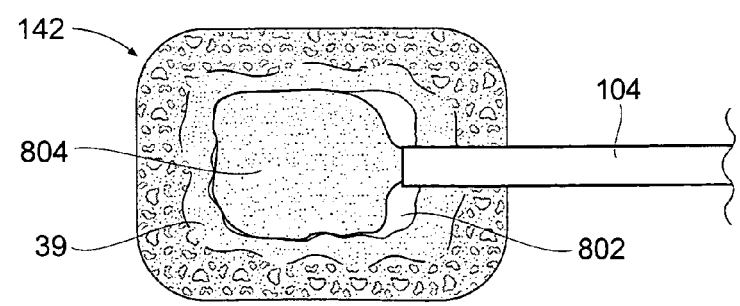
Figure 48A:
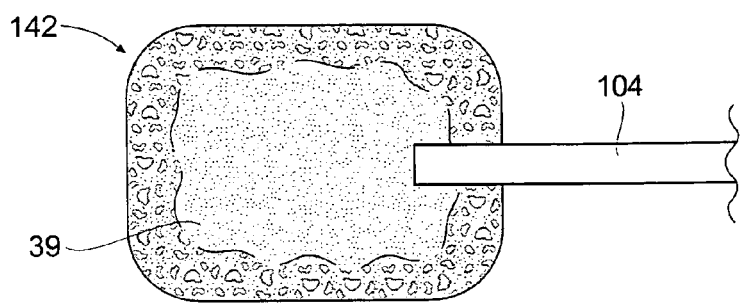
FIGS. 48A–E illustrate an alternative method of creating and filling a void in bone in which a mechanical cutting tool is used to create a void in bone and a first expandable body and then a second expandable body are used to expand and/or further define the void.
Figure 48B:
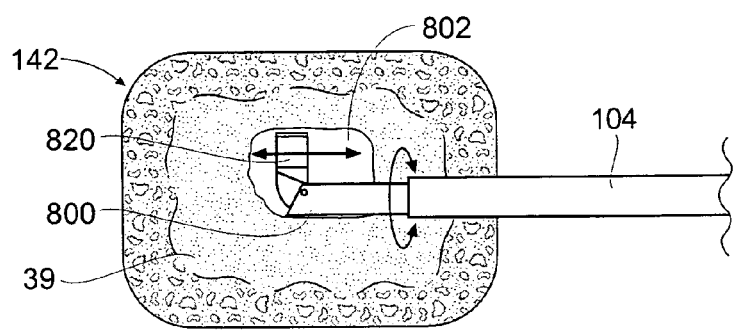
Figure 48C:
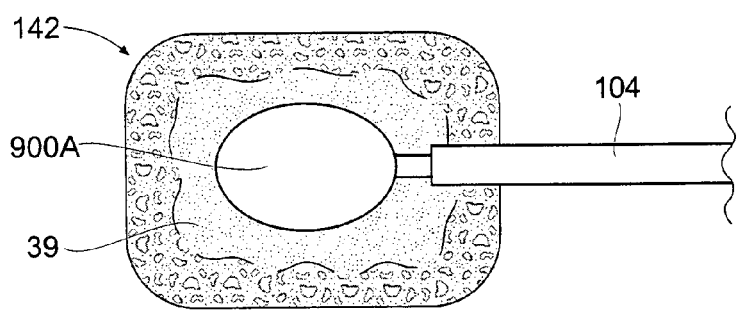
Figure 48D:
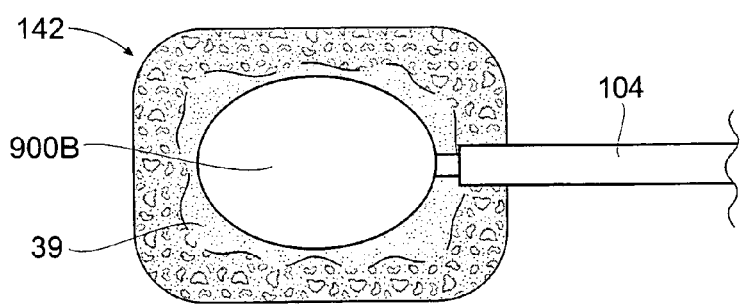
Figure 48E:
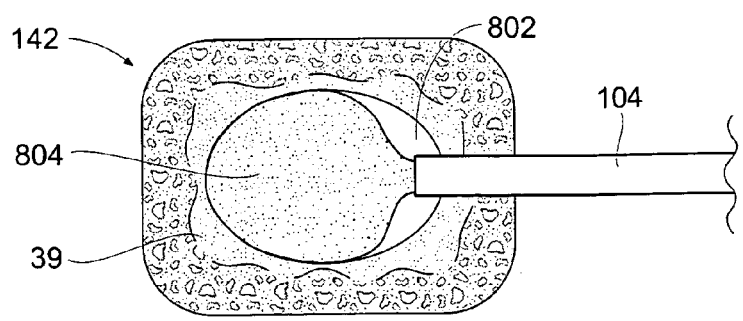

If desired, a second mechanical cutting tool 800B, which may be of a different size and/or configuration from the first mechanical cutting tool 800A, is then introduced prior to filling the void 802 (FIG. 46D). The cutting tip 820B is manipulated in a series of longitudinal and/or rotational movements to enlarge and/or otherwise further define the void 802 created by the expandable structure 900 and first cutting tool 800A. The second cutting tool 800B is then removed. A filler material 804 may then be introduced into the void 802 to fill the void 802 (FIG. 46E).

In an alternative method shown in FIGS. 47A–47E, a first mechanical cutting tool 800A is introduced and manipulated in a series of longitudinal and/or rotational movements to create a void 802. The first cutting tool 800A is then removed. An expandable structure 900 is then introduced and expanded to enlarge and/or otherwise further define the void 802 created by the first cutting tool 800A. The expandable structure 900 is then removed.

If desired, a second mechanical cutting tool 800B, which may be of a different size and/or configuration from the first mechanical cutting tool 800A, is then introduced prior to filling the void 802. The cutting tip 820B is manipulated in a series of longitudinal and/or rotational movements to enlarge and/or otherwise further define the void 802 created by the expandable structure 900A and first cutting tool 802A. The second cutting tool 802B is then removed. A filler material 804 may then be introduced into the void 802 to fill the void 802.

Alternatively, as seen in FIGS. 48A–48E, instead of a second mechanical cutting tool, a second expandable structure 900B, is introduced and expanded to enlarge and/or otherwise further define the void created by the first expandable structure 900A and first cutting tool 800A.

We claim:
1. A method of creating a void in bone comprising
   establishing a percutaneous access path leading into a bone, introducing through the access path a tool having a cutting tip that extends radially from the access path to contact bone, manipulating the cutting tip in cancellous bone to create a void in the cancellous bone, withdrawing the tool, introducing a first expandable structure through the access path, the expandable structure being adapted to undergo expansion in cancellous bone to compact cancellous bone to create a void in the cancellous bone, expanding the first expandable structure in the cancellous bone to enlarge or further define the void, withdrawing the first expandable structure, introducing a second expandable structure through the access path, and expanding the second expandable structure in the cancellous bone to enlarge or further define the void.

2. A method according to claim 1, further comprising introducing a filling material into the void.

3. A method according to claim 1, further comprising, withdrawing the second expandable structure.

4. A method according to claim 1 wherein the second expandable structure is of a different size than the first expandable structure.

5. A method according to claim 1 wherein the second expandable structure is of a different configuration than the first expandable structure.

6. A method according to claim 1 wherein the second expandable structure is of the same size and configuration as the first expandable structure.

7. A method according to claim 1 wherein at least one of the first and second expandable structures is a balloon.

8. A method of creating a void in bone comprising establishing a percutaneous access path leading into a bone, introducing through the access path a first tool having a cutting tip that extends radially from the access path to contact bone, manipulating the cutting tip in cancellous bone to create a void in the cancellous bone, withdrawing the first tool, introducing an expandable structure through the access path, the expandable structure being adapted to undergo expansion in cancellous bone to compact cancellous bone to create a void in the cancellous bone, expanding the expandable structure in the cancellous bone to enlarge or further define the void, withdrawing the expandable structure, introducing through the access path a second tool having a cutting tip that extends radially from the access path to contact bone, and manipulating the cutting tip of the second cutting tool in the cancellous bone to enlarge or further define the void.

9. A method according to claim 8, further comprising introducing a filling material into the void.

10. A method according to claim 8 wherein the cutting tip of the second tool is of a different size than the cutting tip of the first tool.

11. A method according to claim 8 wherein the cutting tip of the second tool is of a different configuration than the cutting tip of the first tool.

12. A method according to claim 8 wherein the cutting tip of the second tool is of the same size and configuration as the cutting tip of the first tool.

13. A method according to claim 8 wherein the expandable structure is a balloon.

14. A method of creating a void in bone comprising establishing a percutaneous access path leading into a bone, introducing through the access path a first tool having a cutting tip that extends radially from the access path to contact bone, manipulating the cutting tip of the first tool in cancellous bone to create a void in the cancellous bone, withdrawing the first tool, introducing through the access path a second tool having a cutting tip that extends radially from the access path to contact bone, manipulating the cutting tip of the second tool in the cancellous bone to enlarge or further define the void, withdrawing the second tool, introducing an expandable structure through the access path, the expandable structure being adapted to undergo expansion in cancellous bone to compact cancellous bone to create a void in the cancellous bone, and expanding the expandable structure in the cancellous bone to enlarge or further define the void.

15. A method according to claim 14, further comprising withdrawing the expandable structure.

16. A method according to claim 14, further comprising introducing a filling material into the void.

17. A method according to claim 14 wherein the expandable structure is a balloon.

18. A method according to claim 14 wherein the cutting tip of the second tool is of a different size than the cutting tip of the first tool.

19. A method according to claim 14 wherein the cutting tip of the second tool is of a different configuration than the cutting tip of the first tool.

20. A method according to claim 14 wherein the cutting tip of the second tool is of the same size and configuration as the cutting tip of the first tool.

21. A method of creating a void in bone comprising establishing a percutaneous access path leading into a bone, introducing a first expandable structure through the access path, the first expandable structure being adapted to undergo expansion in cancellous bone to compact cancellous bone to create a void in the cancellous bone, expanding the first expandable structure in cancellous bone to create a void, withdrawing the first expandable structure, introducing a second expandable structure through the access path, the second expandable structure being adapted to undergo expansion in cancellous bone to compact cancellous bone to create a void in the cancellous bone, expanding the second expandable structure in the cancellous bone to enlarge or further define the void, withdrawing the second expandable structure, introducing through the access path a tool having a cutting tip that extends radially from the access path to contact bone, and manipulating the cutting tip in the cancellous bone to enlarge or further define the void.

22. A method according to claim 21, further comprising introducing a filling material into the void.

23. A method according to claim 21 wherein the second expandable structure is of a different size than the first expandable structure.

24. A method according to claim 21 wherein the second expandable structure is of a different configuration than the first expandable structure.

25. A method according to claim 21 wherein the second expandable structure is of the same size and configuration as the first expandable structure.

26. A method according to claim 21 wherein at least one of the first and second expandable structures is a balloon.

27. A method of creating a void in bone comprising
establishing a percutaneous access path leading into a bone,
introducing a first expandable structure through the access path, the first expandable structure being adapted to undergo expansion in cancellous bone to compact cancellous bone to create a void in the cancellous bone,
expanding the first expandable structure in cancellous bone to create a void,
withdrawing the first expandable structure,
introducing through the access path a tool having a cutting tip that extends radially from the access path to contact bone,
manipulating the cutting tip in the cancellous bone to enlarge or further define the void,
withdrawing the tool,
introducing a second expandable structure through the access path, the second expandable structure being adapted to undergo expansion in cancellous bone to compact cancellous bone to create a void in the cancellous bone, and
expanding the second expandable structure in cancellous bone to enlarge or further define the void.

28. A method according to claim 27, further comprising introducing a filling material into the void.

29. A method according to claim 27 wherein the second expandable structure is of the same size and configuration as the first expandable structure.

30. A method according to claim 27 wherein the second expandable structure is of a different size from the first expandable structure.

31. A method according to claim 27 wherein the second expandable structure is of a different configuration from the first expandable structure.

32. A method according to claim 27 wherein at least one of the first and second expandable structures is a balloon.

33. A method according to claim 27 withdrawing the second expandable structure.

34. A method of creating a void in bone comprising
establishing a percutaneous access path leading into a bone,
introducing an expandable structure through the access path, the expandable structure being adapted to undergo expansion in cancellous bone to compact cancellous bone to create a void in the cancellous bone,
expanding the expandable structure,
introducing through the access path a first tool having a cutting tip that extends radially from the access path to contact bone,
manipulating the cutting tip in the cancellous bone to enlarge or further define the void,
withdrawing the first tool,
introducing through the access path a second tool having a cutting tip that extends radially from the access path to contact bone, and
manipulating the cutting tip of the second tool in the cancellous bone to enlarge or further define the void.

35. A method according to claim 34, further comprising introducing a filling material into the void.

36. A method according to claim 34 wherein the expandable structure is a balloon.

37. A method according to claim 34 wherein the cutting tip of the second tool is of a different size than the tip of the first tool.

38. A method according to claim 34 wherein the cutting tip of the second tool is of a different configuration than the tip of the first tool.

39. A method according to claim 34 wherein the cutting tip of the second tool is of the same size and configuration as the cutting tip of the first tool.

* * * * *

UNITED STATES PATENT AND TRADEMARK OFFICE
CERTIFICATE OF CORRECTION

PATENT NO. : 6,923,813 B2
DATED : August 2, 2005
INVENTOR(S) : Frank M. Phillips et al.

It is certified that error appears in the above-identified patent and that said Letters Patent is hereby corrected as shown below:

Title page,
Item [56], References Cited, U.S. PATENT DOCUMENTS, "3,181,533" reference, delete "Health" and substitute -- Heath --.

Signed and Sealed this

Thirty-first Day of January, 2006

JON W. DUDAS
*Director of the United States Patent and Trademark Office*